(12) United States Patent
Saar et al.

(10) Patent No.: US 12,053,601 B2
(45) Date of Patent: *Aug. 6, 2024

(54) REDUCED OPERATION FORCE INFLATOR

(71) Applicant: Edwards Lifesciences Corporation, Irvine, CA (US)

(72) Inventors: Tomer Saar, Pardes Hanna-Karkur (IL); Michael Bukin, Pardes Hanna (IL); Dudu Haimovich, Ramat Yishai (IL); Roee Haimovich, Migdal Haemek (IL); Ohad Yakobovitch, Hiafa (IL)

(73) Assignee: EDWARDS LIFESCIENCES CORPORATION, Irvine, CA (US)

( * ) Notice: Subject to any disclaimer, the term of this patent is extended or adjusted under 35 U.S.C. 154(b) by 835 days.

This patent is subject to a terminal disclaimer.

(21) Appl. No.: 17/111,924

(22) Filed: Dec. 4, 2020

(65) Prior Publication Data

US 2021/0085952 A1 Mar. 25, 2021

Related U.S. Application Data

(63) Continuation of application No. 16/031,448, filed on Jul. 10, 2018, now Pat. No. 10,857,334.

(Continued)

(51) Int. Cl.
*A61M 39/22* (2006.01)
*A61F 2/24* (2006.01)
(Continued)

(52) U.S. Cl.
CPC ..... *A61M 25/10182* (2013.11); *A61F 2/2433* (2013.01); *A61M 25/10186* (2013.11);
(Continued)

(58) Field of Classification Search
CPC .......... A61M 2005/3128; A61M 2005/31598; A61M 25/10182; A61M 25/1018;
(Continued)

(56) References Cited

U.S. PATENT DOCUMENTS 519,297 A 5/1894 Bauer
3,685,514 A * 8/1972 Cheney ............ A61M 5/31596
604/90

(Continued)

FOREIGN PATENT DOCUMENTS

DE 19532846 A1 3/1997
DE 19907646 A1 8/2000
(Continued)

OTHER PUBLICATIONS

International Search Report for International Application No. PCT/US2018/041744, completed Dec. 5, 2018.

*Primary Examiner* — Quynh-Nhu H. Vu
(74) *Attorney, Agent, or Firm* — Calfee, Halter & Griswold LLP; Joel B. German

(57) ABSTRACT

Disclosed herein are inflators and methods of using the inflators for inflating inflatable devices, such as balloons, used in medical procedures. Such procedures include angioplasty and the transcatheter delivery of prosthetic heart valves and stents. The inflators overcome the resistances typically generated during such procedures and reduces the force required to fully inflate the balloon.

18 Claims, 16 Drawing Sheets

Related U.S. Application Data

(60) Provisional application No. 62/531,787, filed on Jul. 12, 2017.

(51) Int. Cl.
*A61M 25/10* (2013.01)
*A61F 2/958* (2013.01)
*A61M 5/31* (2006.01)
*A61M 5/315* (2006.01)

(52) U.S. Cl.
CPC .............. *A61M 39/22* (2013.01); *A61F 2/958* (2013.01); *A61M 2005/3128* (2013.01); *A61M 2005/31598* (2013.01)

(58) Field of Classification Search
CPC ...... A61M 25/10181; A61M 25/10184; A61M 25/10185; A61M 25/10186; A61M 39/22; A61F 2/2433; A61F 2/958
See application file for complete search history.

(56) References Cited

U.S. PATENT DOCUMENTS

| | | |
|---|---|---|
| 4,035,849 A | 7/1977 | Angell et al. |
| 4,085,749 A | 4/1978 | Chambron |
| 4,476,866 A * | 10/1984 | Chin ............... A61M 25/10182 604/920 |
| 4,592,340 A | 6/1986 | Boyles |
| 4,758,223 A | 7/1988 | Rydell |
| 4,919,121 A | 4/1990 | Rydell et al. |
| 4,955,895 A | 9/1990 | Sugiyama et al. |
| 4,994,077 A | 2/1991 | Dobben |
| 5,059,177 A | 10/1991 | Towne et al. |
| 5,085,249 A | 2/1992 | Dragan et al. |
| 5,176,698 A | 1/1993 | Burns et al. |
| 5,192,297 A | 3/1993 | Hull |
| 5,266,073 A | 11/1993 | Wall |
| 5,298,024 A * | 3/1994 | Richmond ......... A61M 5/31596 604/88 |
| 5,325,845 A | 7/1994 | Adair |
| 5,358,496 A | 10/1994 | Ortiz et al. |
| 5,411,552 A | 5/1995 | Andersen et al. |
| 5,554,185 A | 9/1996 | Block et al. |
| 5,591,195 A | 1/1997 | Taheri et al. |
| 5,599,305 A | 2/1997 | Hermann et al. |
| 5,632,760 A | 5/1997 | Sheiban et al. |
| 5,639,274 A | 6/1997 | Fischell et al. |
| 5,669,879 A * | 9/1997 | Duer ............... A61M 25/10185 604/99.04 |
| 5,728,068 A | 3/1998 | Leone et al. |
| 5,749,890 A | 5/1998 | Shaknovich |
| 5,782,809 A | 7/1998 | Umeno et al. |
| 5,785,682 A * | 7/1998 | Grabenkort ........ A61M 5/31511 604/82 |
| 5,824,044 A | 10/1998 | Quiachon et al. |
| 5,840,081 A * | 11/1998 | Andersen ............... A61F 2/2475 606/108 |
| 5,908,405 A | 6/1999 | Imran et al. |
| 5,916,147 A | 6/1999 | Boury |
| 5,961,536 A | 10/1999 | Mickley et al. |
| 5,968,068 A | 10/1999 | Dehdashtian et al. |
| 6,019,777 A | 2/2000 | Mackenzie |
| 6,027,510 A | 2/2000 | Alt |
| 6,033,381 A | 3/2000 | Kontos |
| 6,143,016 A | 11/2000 | Bleam et al. |
| 6,162,208 A | 12/2000 | Hipps |
| 6,168,614 B1 | 1/2001 | Andersen et al. |
| 6,174,327 B1 | 1/2001 | Mertens et al. |
| 6,217,585 B1 | 4/2001 | Houser et al. |
| 6,235,050 B1 | 5/2001 | Quiachon et al. |
| 6,251,092 B1 | 6/2001 | Qin et al. |
| 6,379,372 B1 | 4/2002 | Dehdashtian et al. |
| 6,383,171 B1 | 5/2002 | Gifford et al. |
| 6,454,799 B1 | 9/2002 | Schreck |
| 6,458,153 B1 | 10/2002 | Bailey et al. |
| 6,461,382 B1 | 10/2002 | Cao |
| 6,471,672 B1 | 10/2002 | Brown et al. |
| 6,500,147 B2 | 12/2002 | Omaleki et al. |
| 6,514,228 B1 | 2/2003 | Hamilton et al. |
| 6,527,979 B2 | 3/2003 | Constantz et al. |
| 6,575,937 B2 * | 6/2003 | Hansen ........... A61M 25/10182 604/181 |
| 6,579,305 B1 | 6/2003 | Lashinski |
| 6,582,462 B1 | 6/2003 | Andersen et al. |
| 6,652,578 B2 | 11/2003 | Bailey et al. |
| 6,730,118 B2 | 5/2004 | Spenser et al. |
| 6,733,525 B2 | 5/2004 | Yang et al. |
| 6,764,504 B2 | 7/2004 | Wang et al. |
| 6,767,362 B2 | 7/2004 | Schreck |
| 6,830,584 B1 | 12/2004 | Seguin |
| 6,893,460 B2 | 5/2005 | Spenser et al. |
| 6,908,481 B2 | 6/2005 | Cribier |
| 7,011,094 B2 | 3/2006 | Rapacki et al. |
| 7,018,406 B2 | 3/2006 | Seguin et al. |
| 7,018,408 B2 | 3/2006 | Bailey et al. |
| 7,137,993 B2 | 11/2006 | Acosta et al. |
| 7,276,084 B2 | 10/2007 | Yang et al. |
| 7,318,278 B2 | 1/2008 | Zhang et al. |
| 7,320,702 B2 | 1/2008 | Hammersmark et al. |
| 7,320,704 B2 | 1/2008 | Lashinski et al. |
| 7,374,571 B2 | 5/2008 | Pease et al. |
| 7,393,360 B2 | 7/2008 | Spenser et al. |
| 7,435,257 B2 | 10/2008 | Lashinski et al. |
| 7,510,575 B2 | 3/2009 | Spenser et al. |
| 7,585,321 B2 | 9/2009 | Cribier |
| 7,594,926 B2 | 9/2009 | Linder et al. |
| 7,597,709 B2 | 10/2009 | Goodin |
| 7,618,446 B2 | 11/2009 | Andersen et al. |
| 7,780,723 B2 | 8/2010 | Taylor |
| 7,785,366 B2 | 8/2010 | Maurer et al. |
| 7,828,765 B2 * | 11/2010 | Hallahan ............... A61D 1/02 604/82 |
| 7,959,661 B2 | 6/2011 | Hijlkema et al. |
| 8,029,556 B2 | 10/2011 | Rowe |
| 8,167,932 B2 | 5/2012 | Bourang et al. |
| RE43,882 E | 12/2012 | Hopkins et al. |
| 8,449,606 B2 | 5/2013 | Eliasen et al. |
| 8,475,523 B2 | 7/2013 | Duffy |
| 8,568,472 B2 | 10/2013 | Marchand et al. |
| 9,061,119 B2 | 6/2015 | Le et al. |
| 9,119,716 B2 | 9/2015 | Lee et al. |
| 9,795,477 B2 | 10/2017 | Tran et al. |
| 10,857,334 B2 * | 12/2020 | Saar ..................... A61M 39/22 |
| 2001/0002445 A1 | 5/2001 | Vesely |
| 2001/0007082 A1 | 7/2001 | Dusbabek et al. |
| 2002/0032481 A1 | 3/2002 | Gabbay |
| 2002/0058995 A1 | 5/2002 | Stevens |
| 2002/0165461 A1 | 11/2002 | Hayzelden et al. |
| 2003/0040792 A1 | 2/2003 | Gabbay |
| 2003/0050694 A1 | 3/2003 | Yang et al. |
| 2003/0120341 A1 | 6/2003 | Shennib et al. |
| 2004/0093061 A1 | 5/2004 | Acosta et al. |
| 2004/0133263 A1 | 7/2004 | Dusbabek et al. |
| 2004/0143197 A1 | 7/2004 | Soukup et al. |
| 2004/0186563 A1 | 9/2004 | Lobbi |
| 2004/0186565 A1 | 9/2004 | Schreck |
| 2004/0260389 A1 | 12/2004 | Case et al. |
| 2005/0080474 A1 | 4/2005 | Andreas et al. |
| 2005/0096736 A1 | 5/2005 | Osse et al. |
| 2005/0137689 A1 | 6/2005 | Salahieh et al. |
| 2005/0149160 A1 | 7/2005 | McFerran |
| 2005/0203614 A1 | 9/2005 | Forster et al. |
| 2005/0203617 A1 | 9/2005 | Forster et al. |
| 2005/0245894 A1 | 11/2005 | Zadno-Azizi |
| 2006/0025857 A1 | 2/2006 | Bergheim et al. |
| 2006/0282150 A1 | 12/2006 | Olson et al. |
| 2007/0005131 A1 | 1/2007 | Taylor |
| 2007/0073389 A1 | 3/2007 | Bolduc et al. |
| 2007/0088431 A1 | 4/2007 | Bourang et al. |
| 2007/0112422 A1 | 5/2007 | Dehdashtian |
| 2007/0203575 A1 | 8/2007 | Forster et al. |
| 2007/0219612 A1 | 9/2007 | Andreas et al. |
| 2007/0239254 A1 | 10/2007 | Chia et al. |

(56) References Cited

U.S. PATENT DOCUMENTS

| | | |
|---|---|---|
| 2007/0244546 A1 | 10/2007 | Francis |
| 2007/0265700 A1 | 11/2007 | Eliasen et al. |
| 2008/0065011 A1 | 3/2008 | Marchand et al. |
| 2008/0125853 A1 | 5/2008 | Bailey et al. |
| 2008/0294230 A1 | 11/2008 | Parker |
| 2009/0024428 A1 | 1/2009 | Hudock, Jr. |
| 2009/0069889 A1 | 3/2009 | Suri et al. |
| 2009/0138079 A1 | 5/2009 | Tuval et al. |
| 2009/0157175 A1 | 6/2009 | Benichou |
| 2009/0192585 A1 | 7/2009 | Bloom et al. |
| 2009/0228093 A1 | 9/2009 | Taylor et al. |
| 2009/0276040 A1 | 11/2009 | Rowe et al. |
| 2009/0281619 A1 | 11/2009 | Le et al. |
| 2009/0299456 A1 | 12/2009 | Melsheimer |
| 2009/0319037 A1 | 12/2009 | Rowe et al. |
| 2010/0030318 A1 | 2/2010 | Berra |
| 2010/0036472 A1 | 2/2010 | Papp |
| 2010/0036473 A1 | 2/2010 | Roth |
| 2010/0049313 A1 | 2/2010 | Alon et al. |
| 2010/0076402 A1 | 3/2010 | Mazzone et al. |
| 2010/0076541 A1 | 3/2010 | Kumoyama |
| 2010/0082089 A1 | 4/2010 | Quadri et al. |
| 2010/0094394 A1 | 4/2010 | Beach et al. |
| 2010/0121425 A1 | 5/2010 | Shimada |
| 2010/0145431 A1 | 6/2010 | Wu et al. |
| 2010/0161036 A1 | 6/2010 | Pintor et al. |
| 2010/0174363 A1 | 7/2010 | Castro |
| 2010/0198347 A1 | 8/2010 | Zakay et al. |
| 2010/0274344 A1 | 10/2010 | Dusbabek et al. |
| 2010/0286513 A1 | 11/2010 | Pollard, Jr. et al. |
| 2011/0015729 A1 | 1/2011 | Jimenez et al. |
| 2011/0054395 A1 | 3/2011 | O'Dea et al. |
| 2011/0054596 A1 | 3/2011 | Taylor |
| 2011/0137331 A1 | 6/2011 | Walsh et al. |
| 2011/0160846 A1 | 6/2011 | Bishop et al. |
| 2012/0123529 A1 | 5/2012 | Levi et al. |
| 2012/0239142 A1 | 9/2012 | Liu et al. |
| 2013/0030519 A1 | 1/2013 | Tran et al. |
| 2013/0317598 A1 | 11/2013 | Rowe et al. |
| 2014/0296962 A1 | 10/2014 | Cartledge et al. |
| 2017/0065415 A1 | 3/2017 | Rupp et al. |
| 2018/0153689 A1 | 6/2018 | Maimon et al. |
| 2018/0344456 A1 | 12/2018 | Barash et al. |

FOREIGN PATENT DOCUMENTS

| | | |
|---|---|---|
| EP | 0592410 B1 | 10/1995 |
| EP | 0850607 A1 | 7/1998 |
| EP | 0896156 A2 | 2/1999 |
| FR | 2815844 A1 | 5/2002 |
| WO | 9117720 | 11/1991 |
| WO | 9829057 A1 | 7/1998 |
| WO | 9912483 A1 | 3/1999 |
| WO | 0149213 A2 | 7/2001 |
| WO | 0154625 A1 | 8/2001 |
| WO | 0176510 A2 | 10/2001 |
| WO | 0222054 A1 | 3/2002 |
| WO | 0236048 A1 | 5/2002 |
| WO | 0247575 A2 | 6/2002 |
| WO | 02060352 | 8/2002 |
| WO | 03030776 A2 | 4/2003 |
| WO | 03047468 A1 | 6/2003 |
| WO | 2004019825 A1 | 3/2004 |
| WO | 2005084595 A1 | 9/2005 |
| WO | 2006032051 A2 | 3/2006 |
| WO | 2006111391 A1 | 10/2006 |
| WO | 2006138173 A3 | 3/2007 |
| WO | 2005102015 A3 | 4/2007 |
| WO | 2007047488 A2 | 4/2007 |
| WO | 2007067942 A1 | 6/2007 |
| WO | 2010121076 A2 | 10/2010 |

\* cited by examiner

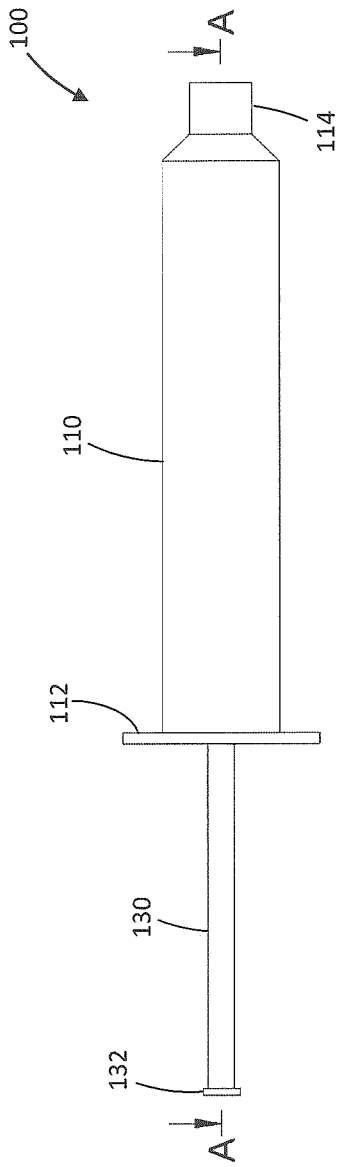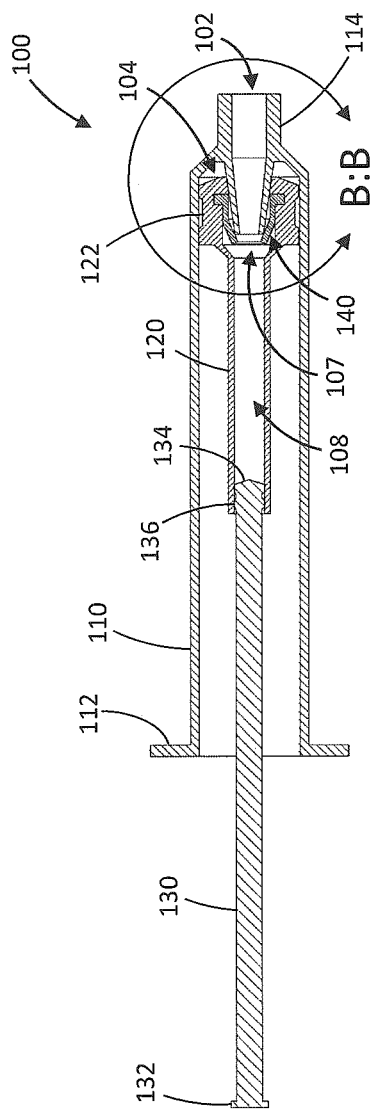

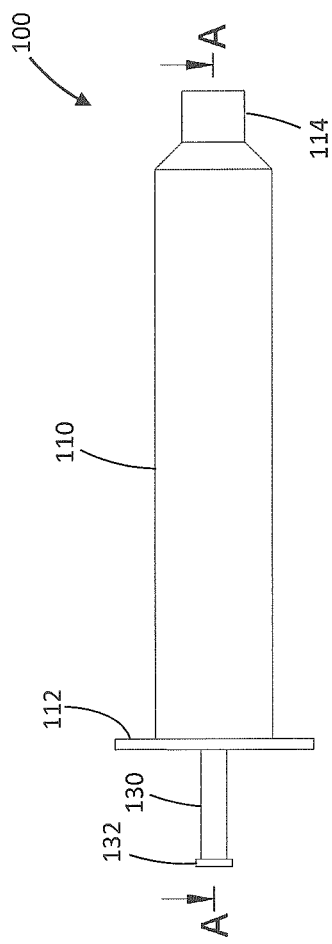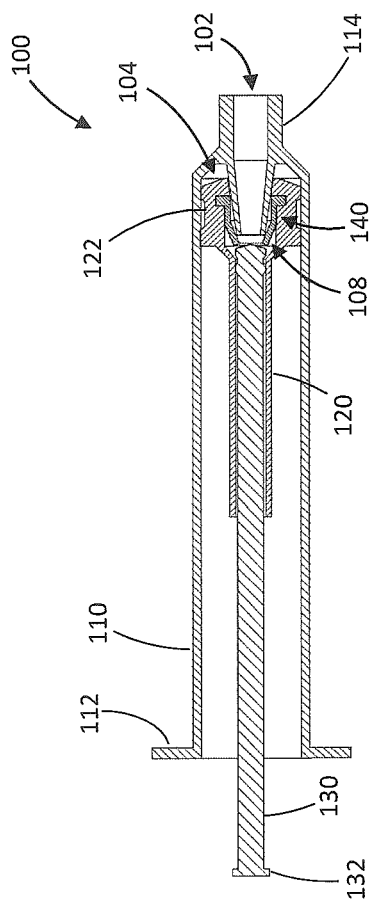
FIG. 4
FIG. 4A

REDUCED OPERATION FORCE INFLATOR

CROSS-REFERENCE TO RELATED APPLICATIONS

The present application claims the benefit of U.S. application Ser. No. 16/031,448, filed on Jul. 10, 2018, and titled REDUCED OPERATION FORCE INFLATOR, which claims the benefit of U.S. Provisional Application Ser. No. 62/531,787, filed on Jul. 12, 2017, and titled REDUCED OPERATION FORCE INFLATOR, the disclosures of which are incorporated herein by reference in their entireties.

TECHNICAL FIELD

The present application relates generally to inflators and in particular to inflators for inflating inflatable devices used in medical procedures, including in the delivery of prosthetic heart valves and stents.

BACKGROUND OF THE INVENTION

Inflatable devices, such as balloons, are used in a broad range of minimally invasive medical procedures. They can be produced in a wide range of diameters, lengths, and shapes suitable for use in a variety of diagnostic and therapeutic procedures, including angioplasty. Balloon catheters are also commonly used to deliver prosthetic medical devices, such as prosthetic heart valves and stents.

Medical devices implanted through a catheter—e.g., prosthetic heart valves and stents—are compressed to a reduced diameter to fit through the catheter during delivery. The devices must then be expanded to their full size to be implanted in the desired location, for example, within a native heart valve of the patient. Some devices are expanded through a direct mechanical means, such as pulling or pushing on an actuation wire that causes the device to expand. Some devices are expanded indirectly with an inflatable device—e.g., a balloon—positioned within the medical device; i.e., the inflatable device expands radially as it is inflated with fluid, thereby causing the medical device to expand. Medical devices capable of being expanded with an inflatable device are known as balloon expandable devices.

Some prior art devices for inflating medical balloons, such as those used in angioplasty and in the transcatheter delivery of prosthetic devices, include syringes. Actuation fluid in the syringe is compressed by actuation of a plunger or piston of the syringe to pressurize and inflate the balloon. The balloon is positioned in the body, and within the balloon expandable device, so that inflation of the balloon expands the device. As the device expands, the actuation force required to further inflate the balloon increases because of resistance caused by the geometry of the balloon expandable device, the surface tension of the balloon, and interaction with the native tissues of the patient.

SUMMARY

Exemplary embodiments of inflators are disclosed herein.

An exemplary inflator includes an inflator body, a first piston, and a second piston. The inflator body has a first piston chamber, an opening protrusion within the first piston chamber, and a nozzle in fluid communication with the first piston chamber. The first piston includes a first piston head and a second piston chamber. The first piston head includes a piston seal, one-way valve, and valve opening. The second piston includes a second piston head and an actuation portion. An inlet of the one-way valve is in fluid communication with the first piston chamber. An outlet of the one-way valve is in fluid communication with the second piston chamber. Movement of the first piston causes the opening protrusion to engage and open the one-way valve.

Another exemplary embodiment of the present disclosure relates to a process for inflating an inflatable device. The process includes providing an inflator in fluid communication with an inflatable device and applying force to an actuation portion of a second piston of the inflator to actuate the inflator to inflate the inflatable device. The inflator includes an inflator body, a first piston, and the second piston. The inflator body has a first piston chamber, an opening protrusion within the first piston chamber, and a nozzle in fluid communication with the first piston chamber. The first piston includes a first piston head and a second piston chamber. The first piston head includes a piston seal, one-way valve, and valve opening. The second piston includes a second piston head and the actuation portion. An inlet of the one-way valve is in fluid communication with the first piston chamber. An outlet of the one-way valve is in fluid communication with the second piston chamber. Movement of the first piston causes the opening protrusion to engage and open the one-way valve.

A further understanding of the nature and advantages of the present invention are set forth in the following description and claims, particularly when considered in conjunction with the accompanying drawings in which like parts bear like reference numerals.

BRIEF DESCRIPTION OF THE DRAWINGS

These and other features and advantages of the present invention will become better understood with regards to the following description and accompanying drawings in which:

FIG. 3 is a side view of inflator of FIG. 1 in a partially discharged condition;

FIG. 3A a cross-section view of the inflator of FIG. 3 along the plane indicated by line A-A in FIG. 3;

FIG. 4 is a side view of inflator of FIG. 1 in a fully discharged condition;

FIG. 4A a cross-section view of the inflator of FIG. 4 along the plane indicated by line A-A in FIG. 4;

DETAILED DESCRIPTION

Figure 1:
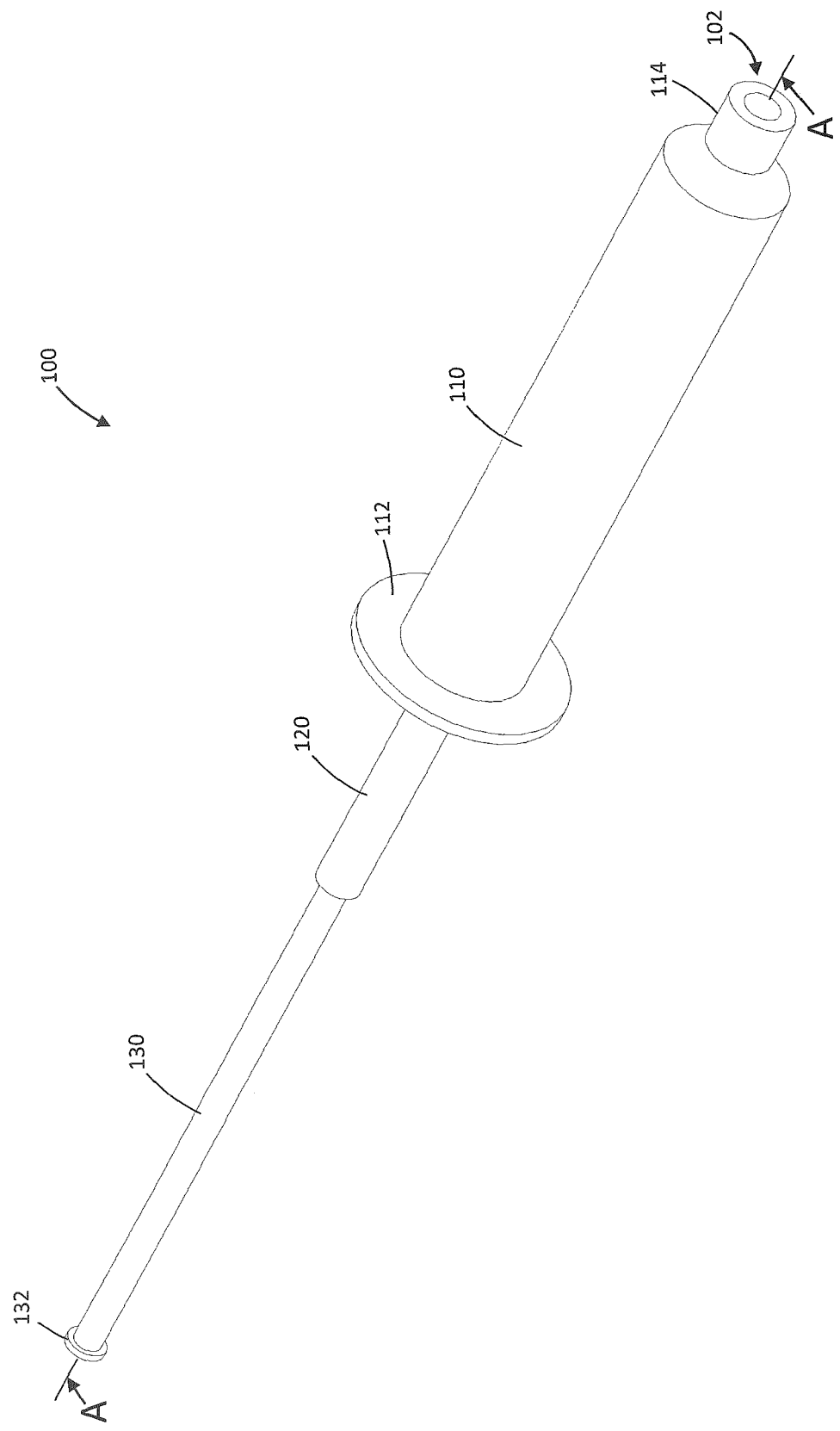
FIG. 1 is a perspective view of an exemplary inflator.
Figure 1A:
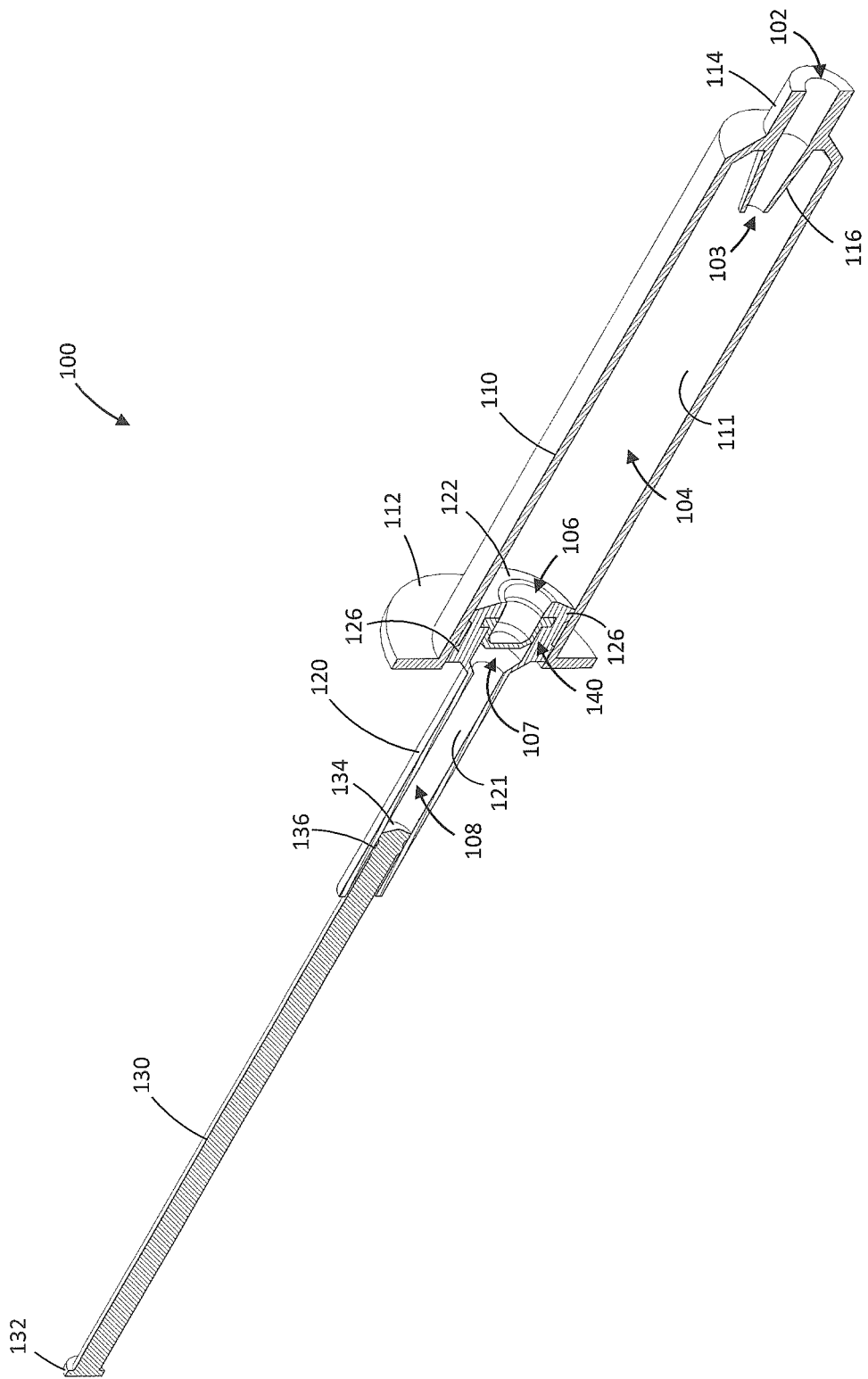
FIG. 1A is a cross-section view of the inflator of FIG. 1 along the plane indicated by the line A-A in FIG. 1.
Figure 2:
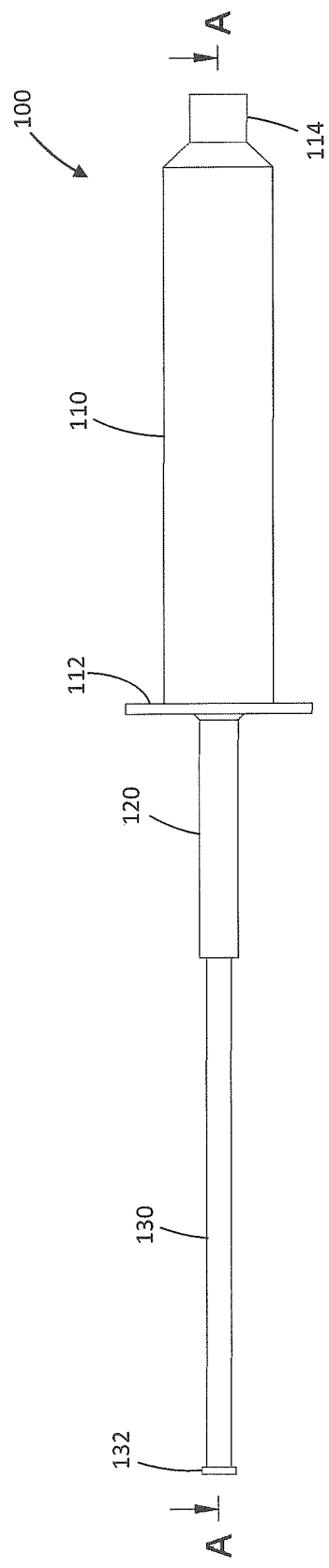
FIG. 2 is a side view of the inflator of FIG. 1 in a fully charged condition.
Figure 2A:
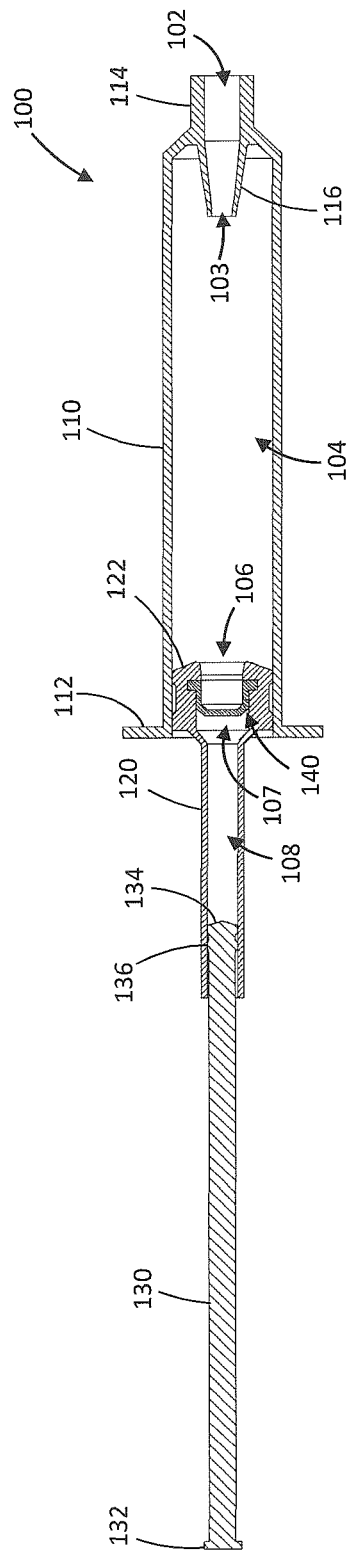
FIG. 2A a cross-section view of the inflator of FIG. 2 along the plane indicated by line A-A in FIG. 2.

As described herein, when one or more components are described as being connected, joined, affixed, coupled, attached, or otherwise interconnected, such interconnection may be direct as between the components or may be indirect such as through the use of one or more intermediary components. Also as described herein, reference to a "member," "component," or "portion" shall not be limited to a single structural member, component, or element but can include an assembly of components, members, or elements. Also as described herein, the terms "substantially" and "about" are defined as at least close to (and includes) a given value or state (preferably within 10% thereof, more preferably within 1% thereof, and most preferably within 0.1% thereof).

A plurality of exemplary embodiments are disclosed herein. The embodiments are described in general here and are described in more detail and with references to the drawings below. An inflator for an inflatable device has a body that forms a first piston bore. The body can have various shapes. In some embodiments, the body can have an elongated cylindrical shape having a round cross-sectional shape. In other embodiments, the body can have an oval cross-sectional shape, a crescent cross-sectional shape, or various other non-cylindrical shapes. A first piston is disposed within the first piston bore, the first piston having a shaft and a piston head configured to form a seal with the first piston bore to enclose a first piston chamber. The arrangement of the first piston is such that movement of the first piston changes the size of the first piston chamber. The body includes a nozzle at one end with an outlet in fluid communication with the first piston chamber such that reduction in the size of the first piston chamber discharges fluid from the first piston chamber.

A second piston bore extends through the length of the first piston. A second piston is disposed within the second piston bore, the second piston having a shaft and a piston head configured to form a seal with the second piston bore to enclose a second piston chamber. An actuation portion is disposed at an end of the shaft of the second piston opposite the piston head. The arrangement of the second piston is such that movement of the second piston changes the size of the second piston chamber.

A one-way valve is disposed within the first piston head. An outlet of the one-way valve is in fluid communication with the second piston chamber, and the inlet of the one-way valve is in fluid communication with the first piston chamber; i.e., under normal conditions, fluid can flow from the first chamber to the second chamber, but not from the second chamber to the first chamber. The orientation of the one-way valve prevents fluid from escaping the second piston chamber when the second piston is compressed. Thus, when force is applied to the actuation portion of the second piston to actuate the inflator, the first and second piston move together in the actuation direction to reduce the size of the first piston chamber, thereby actuating the first piston.

An annular protrusion on the interior of the inflator body has an opening in fluid communication with the outlet of the nozzle. The protrusion is shaped to engage the first piston head, passing through the inlet of the one-way valve to engage the valve. When the first piston is actuated to the bottom of its stroke, the annular protrusion opens the one-way valve, allowing fluid to be discharged from the second piston chamber, thereby allowing the second piston to be actuated. In this way, movement of the first piston opens the one-way valve. Thus, the user applies force to the actuation portion of the second piston to automatically transition between actuation of the first piston and actuation of the second piston.

The second piston has a smaller diameter and consequently a smaller cross-sectional area than the first piston. Thus, the force required to actuate the inflator during actuation of the first piston is greater than the force required to actuate the second piston. The volume of the first and second piston chambers is determined by the diameter of the piston bores and the length of the chambers. Thus, the maximum volume of each chamber may be altered by altering the length and diameter of the same. The volume of the first piston chamber may be greater than, substantially equal to, or less than the volume of the second piston chamber. In some embodiments, the first piston chamber has a volume that is substantially equal to the volume of the second piston chamber, so that substantially the same volume of fluid is displaced by the actuation of the second piston relative to the first piston. In some embodiments, the second piston chamber has less volume than the first piston chamber, so that less fluid is displaced by the actuation of the second piston relative to actuation of the first piston.

Resistance to inflation and expansion causes the force required to actuate the inflator to increase significantly as the device reaches its final expanded condition. Resistance to inflation and expansion can be caused by surface tension of the balloon, geometric resistance of the frame of the expandable device, and other external forces resulting from interaction between the device and the environment, such as a native heart valve. Consequently, the final expansion force required to install the expandable device can be hard to achieve manually in a single continuous motion.

Referring now to FIGS. 1-4A, an exemplary inflator 100 is shown. The inflator 100 has an inflator body 110, a first piston 120, and a second piston 130. The inflator body 110 includes an actuation flange 112 and a nozzle 114. The actuation flange 112 can be located at any position along the exterior of the inflator body 110. The nozzle 114 can be attached to an inflatable device (not shown) to be inflated by the inflator 100. The inflator body 110 encloses a cylindrical first piston bore 111 that is configured to receive the first piston 120. The first piston bore 111 extends along the length of the inflator body 110. An annular opening protrusion 116 is located on the interior of the inflator body 110 and includes a central opening 103 in fluid communication with the outlet 102.

The first piston 120 includes a first piston head 122. A one-way valve 140 having a valve inlet 106 and a valve outlet 107 is incorporated into the first piston head 122. The first piston head 122 includes annular first piston seals 126 that form a seal with the first piston bore 111, thereby forming a first piston chamber 104 when the first piston 120 is inserted into the first piston bore 111. The first piston chamber 104 is in fluid communication with the opening 103 and outlet 102. The first piston 120 encloses a cylindrical second piston bore 121 that is configured to receive the second piston 130. The second piston bore 121 extends along the length of the first piston 120.

The second piston 130 includes an actuation portion 132 and a second piston head 134. The actuation portion 132 may have any form suitable for actuating the second piston 130. The second piston head 134 includes annular second piston seals 136 that form a seal with the second piston bore 122, thereby forming a second piston chamber 108 when the second piston 130 is inserted into the second piston bore 121. Though the illustrated first and second piston chambers are cylindrical and are concentrically aligned, the pistons and piston chambers may be any suitable shape and do not need to be axially aligned.

Figure 3B:
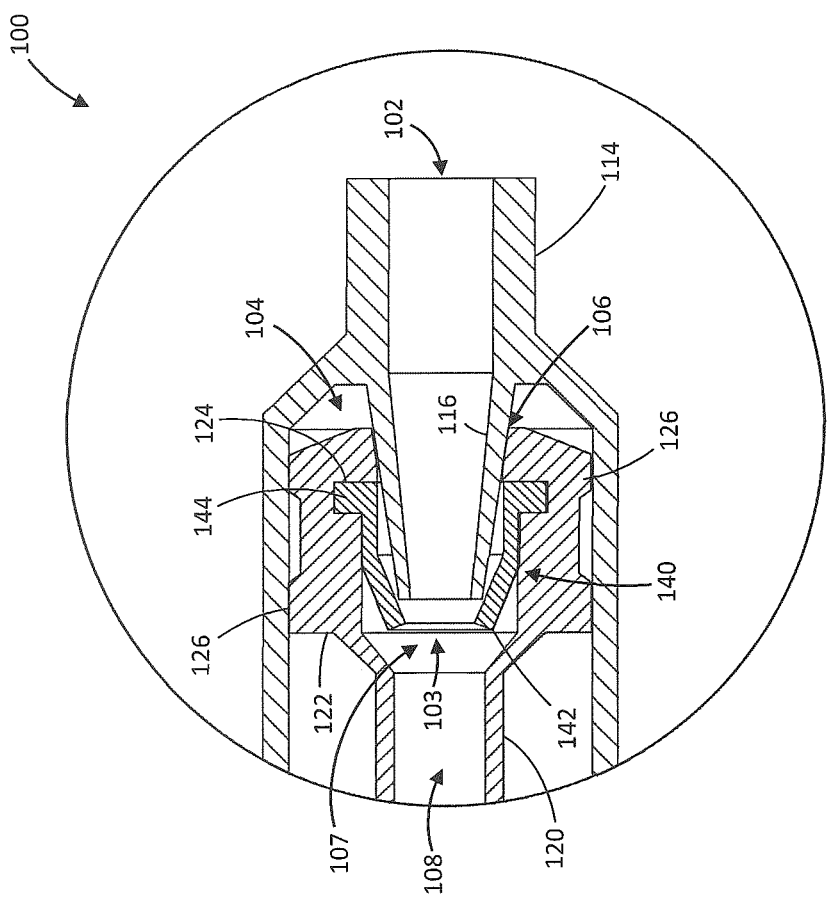
FIG. 3B is an enlarged detail view of the portion of FIG. 3A indicated by the circle B-B.

Referring now to FIG. 3B, the one-way valve 140 includes an opening 142 and a flange 144. The flange 144 is received in an annular groove 124 configured to receive the flange 144 so that the one-way valve is retained within the first piston head 122. In some embodiments, the one-way valve 140 is integrally formed with the first piston 120. The one-way valve 140 is shown as a flexible slit valve, but may be any kind of one-way valve, such as a ball and spring valve, a poppet valve, a flapper valve, an umbrella valve, a mushroom valve, a duck bill valve, or the like. The one-way valve 140 is oriented such that, under normal conditions, the valve 140 prevents flow into the first piston chamber 108 from the second piston chamber 104 and allows flow from the first piston chamber 108 into the second piston chamber 104 through a one-way valve outlet 107. That is, unless the one-way valve 140 is disabled, fluid is only allowed to flow from the first chamber into the second chamber. Also, fluid will only flow from the first chamber to the second chamber when pressure in the first chamber exceeds the pressure in the second chamber.

Referring now to FIGS. 1, 1A, 2, and 2A, the inflator 100 is shown in a fully charged condition. In the fully charged condition, the first and second pistons 120, 130 are withdrawn to starting positions proximate the open ends of the first and second piston bores 111, 121, respectively, and the first and second piston chambers 104, 108 are filled with actuation fluid. The inflator 100 is actuated by applying force to the actuation portion 132 of the second piston 130 while holding the flange 112 of the inflator body 110 to move the first and second pistons 120, 130 thereby compressing the first and second piston chambers 104, 108 to discharge actuation fluid through the outlet 102. The inflator 100 is discharged in two stages, each corresponding to the actuation of one of the two pistons 120, 130.

Referring now to FIGS. 3, 3A, and 3B, the inflator 100 is shown in a partially discharged condition; i.e., after completing the first discharge stage by fully actuating the first piston 120. Discharge of the first piston 120 is accomplished by applying actuation force to the actuation portion 132 of the second piston. During actuation of the first piston 120, the fluid contained in the second piston chamber 108 is trapped by the one-way valve 140, thereby preventing the second piston 130 from actuating.

As can be seen in FIGS. 3, 3A, and 3B, the opening protrusion 116 is shaped to protrude through the valve opening 106 in the first piston head 122 to open the valve opening 142 of the one-way valve 140. That is, the protrusion 116 holds the one-way valve 140 open, allowing fluid to flow in either direction—into or out of the chamber 108. In the illustrated embodiment, the one-way valve 140 is a slit-valve formed from an elastic and flexible material that is capable of being stretched open by the opening protrusion 116 to open the valve opening 142. In certain embodiments, the opening protrusion is a portion of the first piston head that is biased away from the one-way valve with springs that are compressed at the bottom of the stroke of the first piston, thereby allowing the opening protrusion to open the one-way valve. In certain embodiments, the one-way valve is a spring-loaded poppet valve having a poppet that is opened when a protrusion extending from the poppet engages the inflator housing at the bottom of the stroke of the first piston.

Once the opening protrusion 116 (or other structure) has engaged the one-way valve 140 in the first piston head 122, further movement of the pistons 120, 130 causes the opening protrusion 116 to open the one-way valve 140. The one-way valve 140 is fully opened at the end of the actuation stroke of the first piston 120. Opening of the one-way valve 140 allows fluid in the second piston chamber 108 to be discharged, thereby automatically transitioning the inflator 100 between the first and second discharge stages. Thus, both of the first and second pistons 120, 130 of the inflator 100 can be fully actuated (as shown in FIGS. 4 and 4A) in a single application of force to the actuation portion 132 of the second piston 130.

The second piston 130 has a smaller diameter and consequently a smaller cross-sectional area than the first piston 120. Thus, the force required to actuate the inflator 100 during actuation of the first piston 120 is greater than the force required to actuate the second piston 130. The volume of the first and second piston chambers 104, 108 is determined by the diameter of the piston bores 111, 121 and the length of the chambers 104, 108. Thus, the maximum volume of each chamber 104, 108 may be altered by altering the length and diameter of the bores 111, 121. The volume of the first piston chamber 104 may be greater than, substantially equal to, or less than the volume of the second piston chamber 108. In some embodiments, the first piston chamber 104 has a volume that is substantially equal to the volume of the second piston chamber 108 so that substantially the same volume of fluid is displaced by the actuation of the second piston 130 relative to the first piston 120. In some embodiments, the second piston chamber 108 has less volume than the first piston chamber 104, so that less fluid is displaced by the actuation of the second piston 130 relative to actuation of the first piston 120. In certain embodiments, the force required to actuate the second piston 130 is about 5 percent to about 75 percent, or about 5 percent to about 50 percent, or about 5 percent to about 25 percent, or about 10 percent of the force required to actuate the first piston 120.

Figure 5:
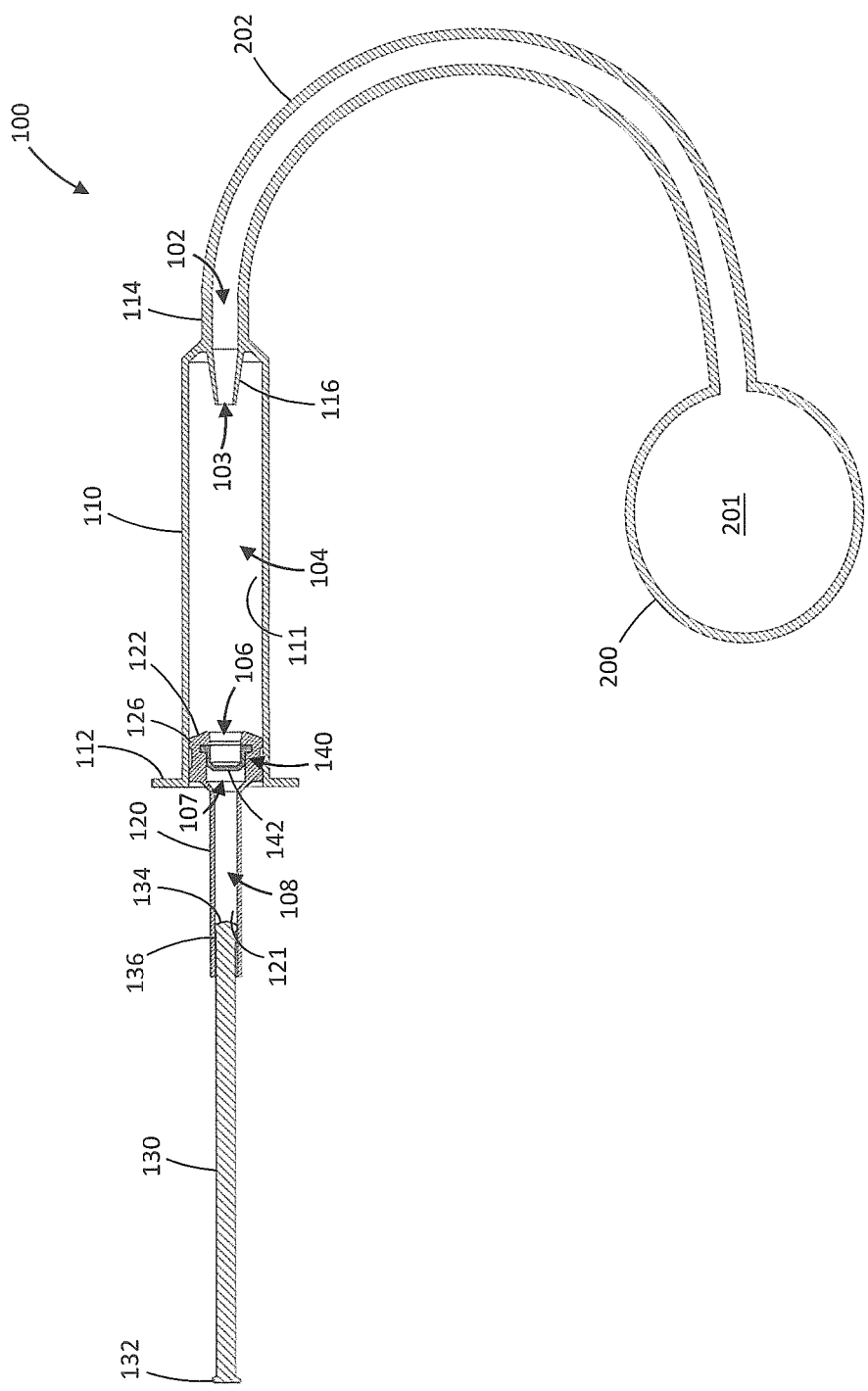
FIG. 5 is a cross-section view of an exemplary inflator in a fully charged condition attached to an inflatable device in a fully deflated condition.
Figure 6:
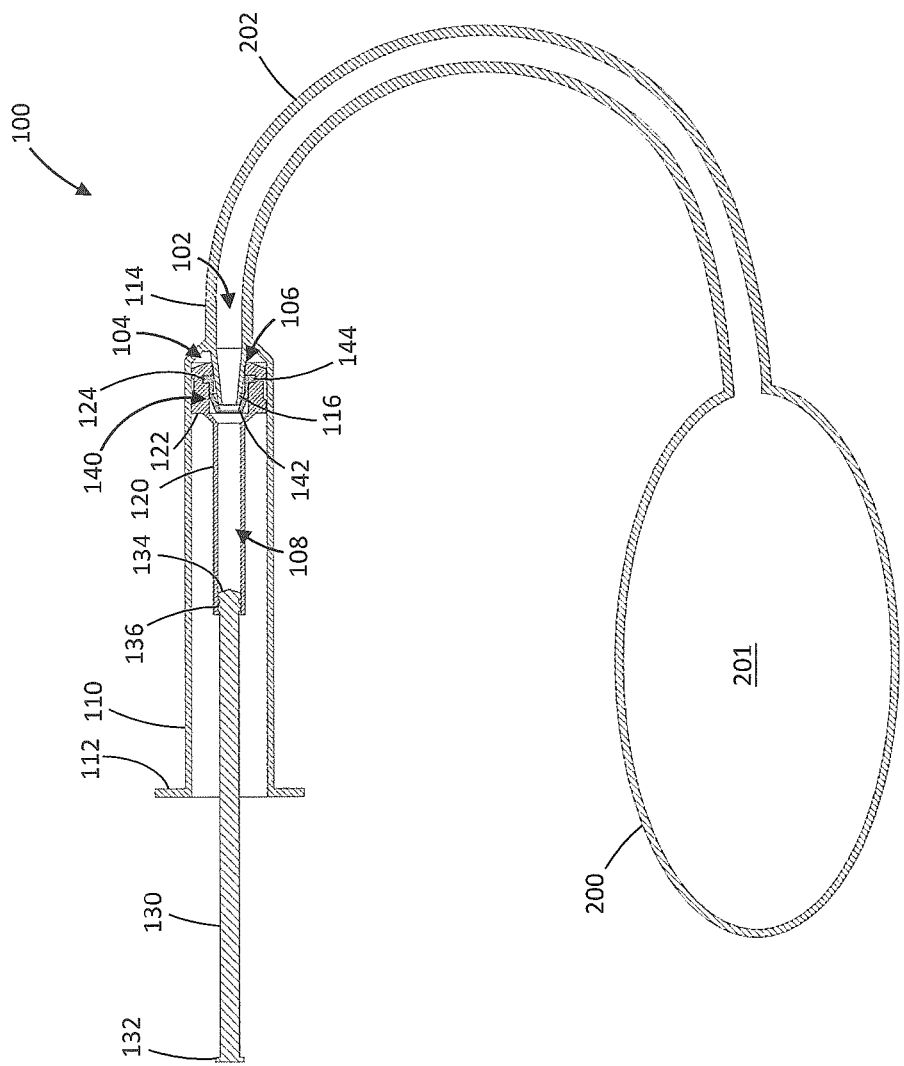
FIG. 6 is a cross-section view of an exemplary inflator in a partially discharged condition attached to an inflatable device in a partially inflated condition.
Figure 7:
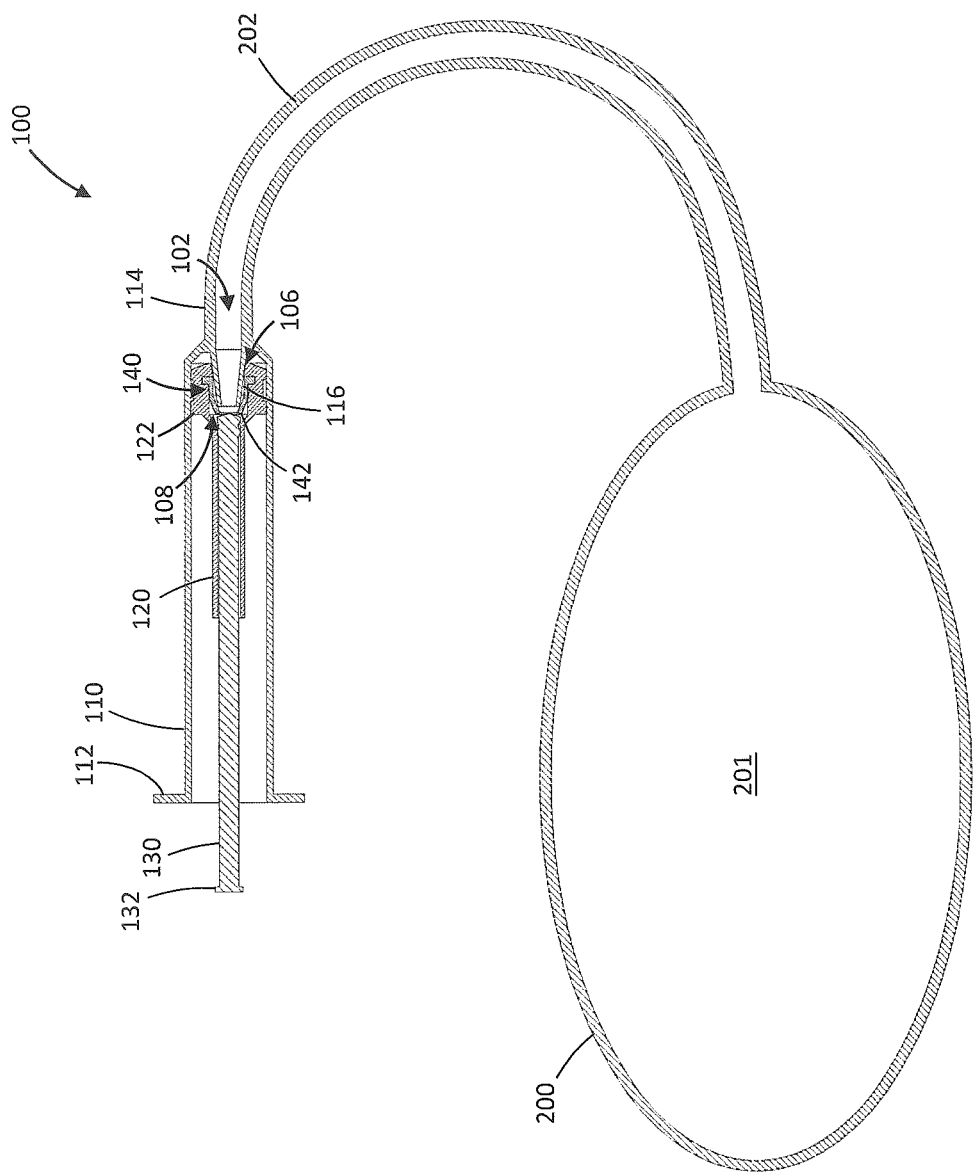
FIG. 7 is a cross-section view of an exemplary inflator in a fully discharged condition attached to an inflatable device in a fully inflated condition.

Referring now to FIGS. 5-7 an exemplary inflator 100 is shown attached to an inflatable device 200 enclosing an inflatable volume 201. The inflator 100 has an inflator body 110, a first piston 120, and a second piston 130. The inflator body 110 includes an actuation flange 112 and a nozzle 114. The actuation flange 112 can be located at any position along the exterior of the inflator body 110. The nozzle 114 is attached to a tube 202 in fluid communication with the inflatable device 200 to be inflated by the inflator 100. In certain embodiments, the tube 202 is integrally formed with the inflator 100. The inflator body 110 encloses a cylindrical first piston bore 111 that is configured to receive the first piston 120. The first piston bore 111 extends along the length of the inflator body 110. An annular opening protrusion 116 is located on the interior of the inflator body 110 and includes a central opening 103 in fluid communication with the outlet 102, the tube 202, and the inflatable volume 201.

The first piston 120 includes a first piston head 122. A one-way valve 140 having a valve inlet 106 and a valve outlet 107 is incorporated into the first piston head 122. The first piston head 122 includes annular first piston seals 226 that form a seal with the first piston bore 111, thereby forming a first piston chamber 104 when the first piston 120 is inserted into the first piston bore 111. The first piston chamber 104 is in fluid communication with the opening 103 and outlet 102. The first piston 120 encloses a cylindrical second piston bore 121 that is configured to receive the second piston 130. The second piston bore 121 extends along the length of the first piston 120.

The second piston 130 includes an actuation portion 132 and a second piston head 134. The actuation portion 132 may have any form suitable for actuating the second piston 130. The second piston head 134 includes annular second piston seals 136 that form a seal with the second piston bore 122, thereby forming a second piston chamber 108 when the second piston 130 is inserted into the second piston bore 121. Though the illustrated first and second piston chambers are cylindrical and are concentrically aligned, the pistons and piston chambers may be any suitable shape and do not need to be axially aligned.

The one-way valve 140 includes an opening 142 and a flange 144. The flange 144 is received in an annular groove 124 configured to receive the flange 144 so that the one-way valve is retained within the first piston head 122. In some embodiments, the one-way valve 140 is integrally formed with the first piston 120. The one-way valve 140 is shown as a flexible slit valve, but may be any kind of one-way valve, such as a ball and spring valve, a poppet valve, a flapper valve, an umbrella valve, a mushroom valve, a duck bill valve, or the like. The one-way valve 140 is oriented such that, under normal conditions, the valve 140 prevents flow into the first piston chamber 108 from the second piston chamber 104, and allows flow from the first piston chamber 108 into the second piston chamber 104 through a one-way valve outlet 107. That is, unless the one-way valve 140 is disabled, fluid is only allowed to flow from the first chamber into the second chamber. Also, fluid will only flow from the first chamber to the second chamber when pressure in the first chamber exceeds the pressure in the second chamber.

Referring now to FIG. 5, the inflator 100 is shown in a fully charged condition. In the fully charged condition, the first and second pistons 120, 130 are withdrawn to starting positions proximate the open ends of the first and second piston bores 111, 121, respectively, and the first and second piston chambers 104, 108 are filled with actuation fluid. The inflator 100 is actuated by applying force to the actuation portion 132 of the second piston 130 while holding the flange 112 of the inflator body 110 to move the first and second pistons 120, 130 thereby compressing the first and second piston chambers 104, 108 to discharge actuation fluid through the outlet 102. The inflator 100 is discharged in two stages, each corresponding to the actuation of one of the two pistons 120, 130.

Referring now to FIG. 6, the inflator 100 is shown in a partially discharged condition; i.e., after completing the first discharge stage by fully actuating the first piston 120. As can be seen by comparing FIGS. 5 and 6, movement from the charged position to the partially discharged position increases the inflated volume 201 of the inflatable device 200. Discharge of the first piston 120 is accomplished by applying actuation force to the actuation portion 132 of the second piston. During actuation of the first piston 120, the fluid contained in the second piston chamber 108 is trapped by the one-way valve 140, thereby preventing the second piston 130 from actuating.

As can be seen in FIG. 6, the opening protrusion 116 is shaped to protrude through the valve opening 106 in the first piston head 122 to open the valve opening 142 of the one-way valve 140. That is, the protrusion 116 holds the one-way valve 140 open, allowing fluid to flow in either direction—into or out of the chamber 108. In the illustrated embodiment, the one-way valve 140 is a slit-valve formed from an elastic and flexible material that is capable of being stretched open by the opening protrusion 116 to open the valve opening 142. In certain embodiments, the opening protrusion is a portion of the first piston head that is biased away from the one-way valve with springs that are compressed at the bottom of the stroke of the first piston, thereby allowing the opening protrusion to open the one-way valve. In certain embodiments, the one-way valve is a spring-loaded poppet valve having a poppet that is opened when a protrusion extending from the poppet engages the inflator housing at the bottom of the stroke of the first piston.

Once the opening protrusion 116 (or other structure) has engaged the one-way valve 140 in the first piston head 122, further movement of the pistons 120, 130 causes the opening protrusion 116 to open the one-way valve 140. The one-way valve 140 is fully opened at the end of the actuation stroke of the first piston 120. Opening of the one-way valve 140 allows fluid in the second piston chamber 108 to be discharged, thereby automatically transitioning the inflator 100 between the first and second discharge stages. Thus, both of the first and second pistons 120, 130 of the inflator 100 can be fully actuated (as shown in FIG. 7) in a single application of force to the actuation portion 132 of the second piston 130. As can be seen by comparing FIGS. 6 and 7, movement from the partially discharged position to the fully discharged position increase the volume 201 of the inflatable device 200.

The second piston 130 has a smaller diameter and consequently a smaller cross-sectional area than the first piston 120. Thus, the force required to actuate the inflator 100 during actuation of the first piston 120 is greater than the force required to actuate the second piston 130. The volume of the first and second piston chambers 104, 108 is determined by the diameter of the piston bores 111, 121 and the length of the chambers 104, 108. Thus, the maximum volume of each chamber 104, 108 may be altered by altering the length and diameter of the bores 111, 121. The volume of the first piston chamber 104 may be greater than, substantially equal to, or less than the volume of the second piston chamber 108. In some embodiments, the first piston chamber 104 has a volume that is substantially equal to the volume of the second piston chamber 108 so that substantially the same volume of fluid is displaced by the actuation of the second piston 130 relative to the first piston 120. In some embodiments, the second piston chamber 108 has less volume than the first piston chamber 104, so that less fluid is displaced by the actuation of the second piston 130 relative to actuation of the first piston 120. In certain embodiments, the force required to actuate the second piston 130 is about 5 percent to about 75 percent, or about 5 percent to about 50 percent, or about 5 percent to about 25 percent, or about 10 percent of the force required to actuate the first piston 120.

Figure 8:
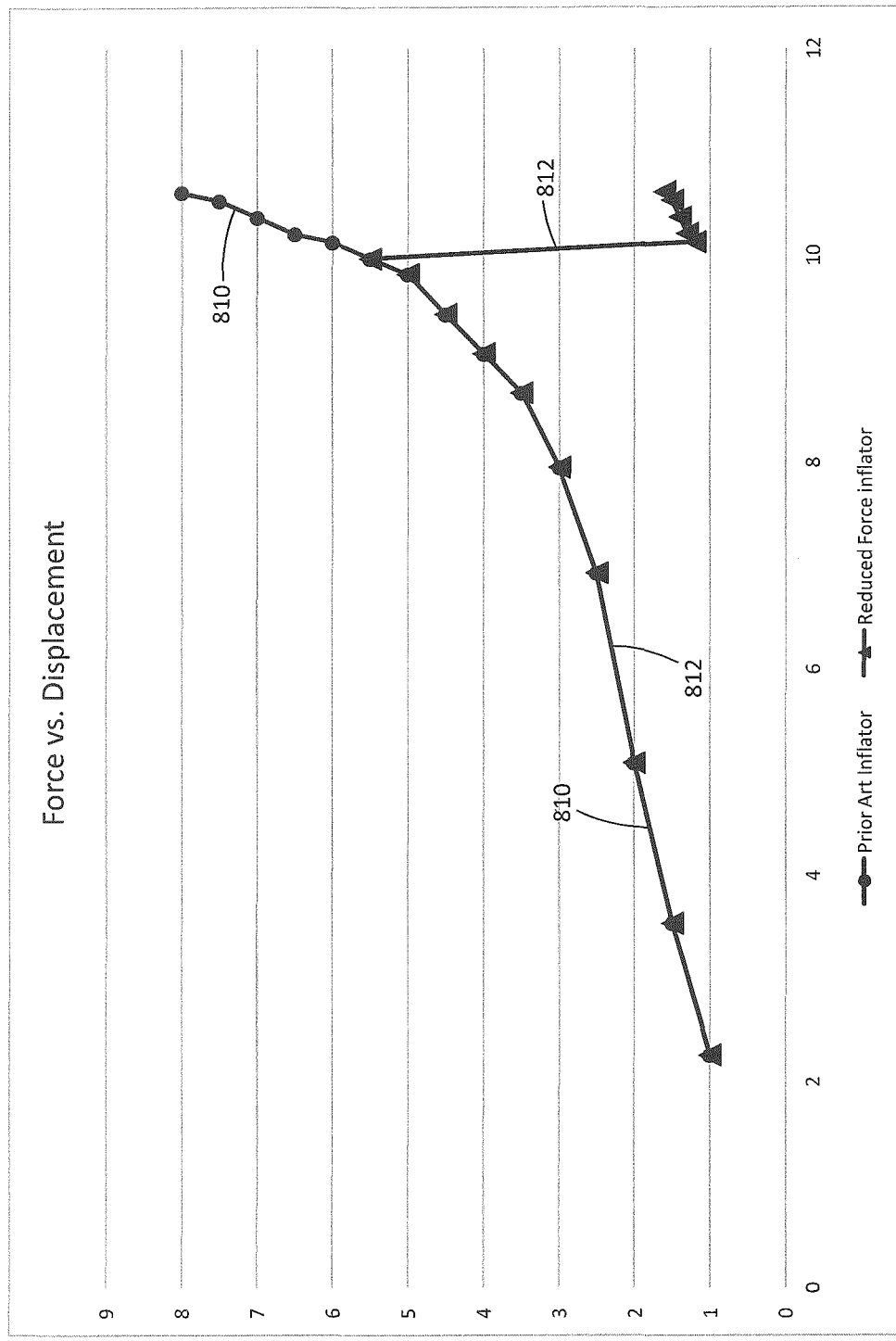
FIG. 8 shows a chart plotting the force applied to an inflatable device against the displacement of an actuation portion of the inflatable device.

Referring now to FIG. 8, a chart illustrating the relationship between the actuation force and the displacement or stroke of an actuation portion of the inflator is shown. A first line 810 indicates the force required to actuate a prior art inflator (e.g., a syringe) relative to the displacement or stroke of an actuation portion of the inflator. A second line 812 indicates the force required to actuate an exemplary inflator relative to the displacement or stroke of an actuation portion of the inflators described above. As can be seen in both inflators, the force required to actuate the inflator to inflate an inflatable device increases as the inflator is actuated because of increasing resistance to inflation from the inflatable device and any other external forces that can also increase (i.e., resistance due to the inflatable device and/or implantable device pressing against native structure). As is clearly shown by the first line 810, the force required to actuate a prior art inflator increases significantly when reaching the fully inflated condition. In contrast, as shown by the second line 812, the force required to actuate the exemplary inflator 100 increases until the inflator transitions from the first piston to the second piston. The transition to the second piston significantly decreases the required actuation force.

Figure 9:
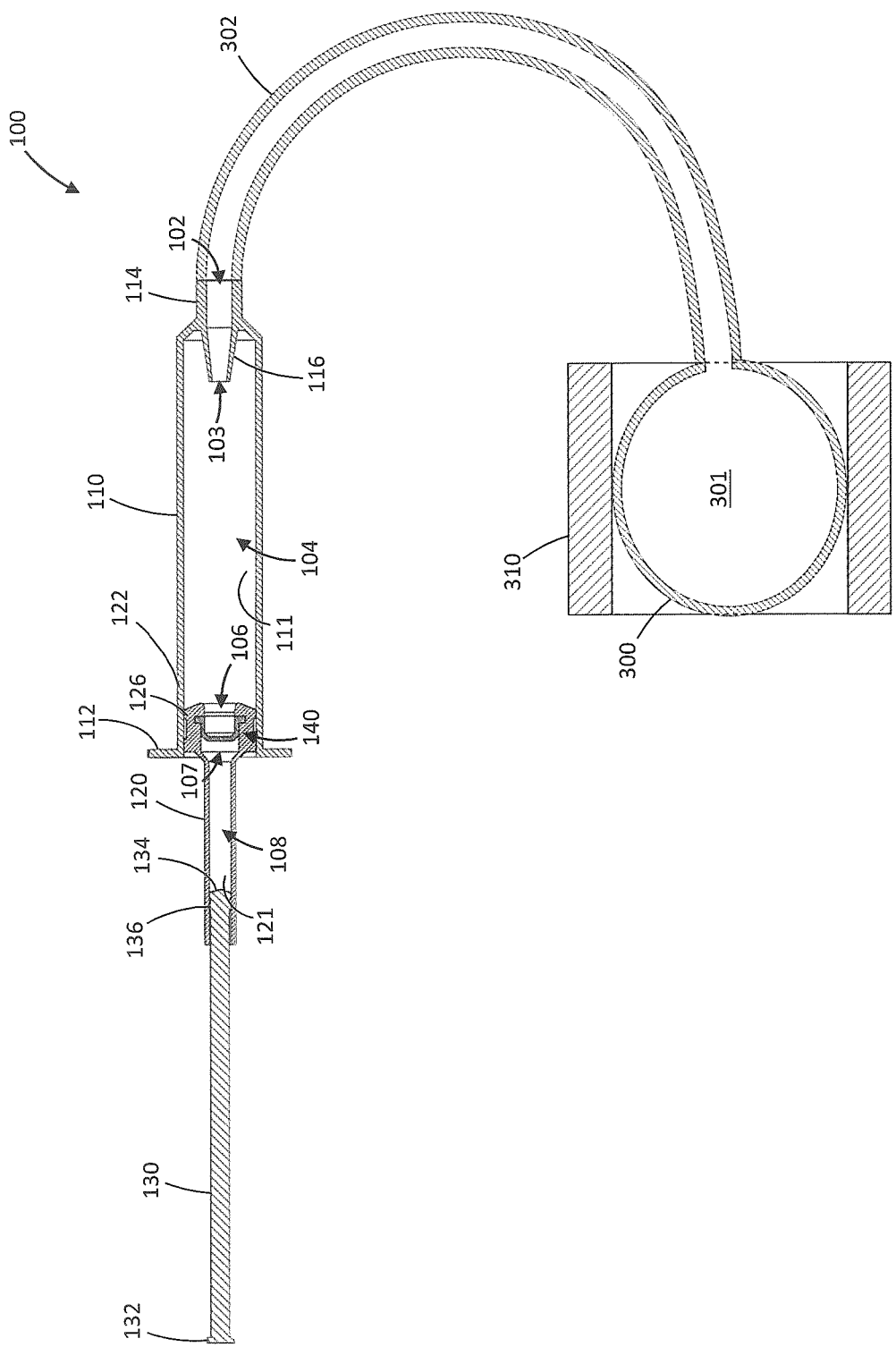
FIG. 9 is a cross-section view an exemplary inflator in a fully charged condition attached to an inflatable device in a fully deflated condition inside of an implantable device.
Figure 10:
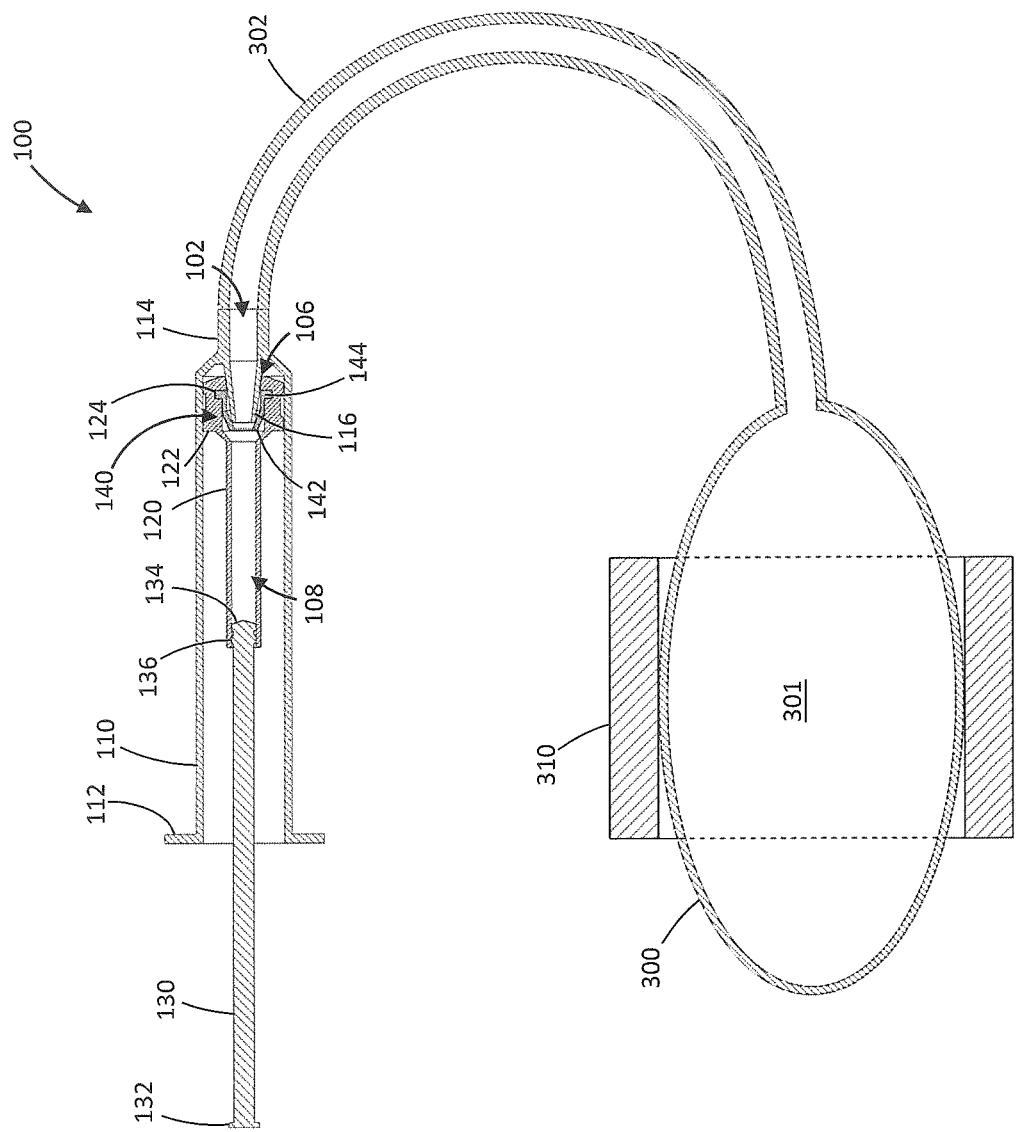
FIG. 10 is a cross-section view of an exemplary inflator in a partially discharged condition attached to an inflatable device in a partially inflated condition inside of an implantable device.
Figure 11:
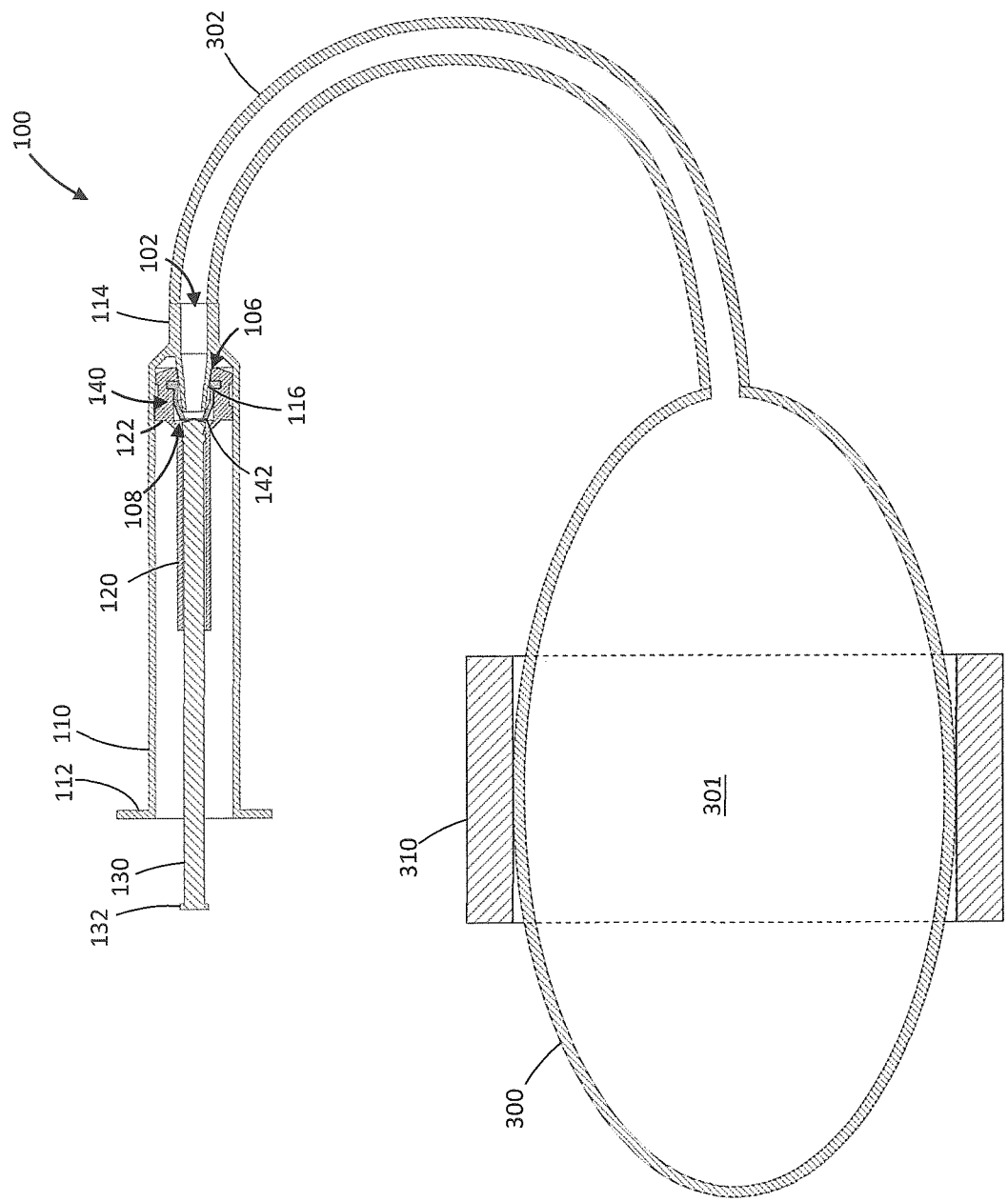
FIG. 11 is a cross-section view of an exemplary inflator in a fully discharged condition attached to an inflatable device in a fully inflated condition inside of an implantable device.

Referring now to FIGS. 9-11 an exemplary inflator 100 is shown attached to an inflatable device 300 enclosing an inflatable volume 301. The inflator 100 has an inflator body 110, a first piston 120, and a second piston 130. The inflator body 110 includes an actuation flange 112 and a nozzle 114. The actuation flange 112 can be located at any position along the exterior of the inflator body 110. The nozzle 114 is attached to a tube 302 in fluid communication with the inflatable device 300 to be inflated by the inflator 100. In certain embodiments, the tube 302 is integrally formed with the inflator 100. The inflatable device 300 is disposed within an expandable medical device 310 to be expanded by inflation of the inflatable device 300. The inflator body 110 encloses a cylindrical first piston bore 111 that is configured to receive the first piston 120. The first piston bore 111 extends along the length of the inflator body 110. An annular opening protrusion 116 is located on the interior of the inflator body 110 and includes a central opening 103 in fluid communication with the outlet 102, the tube 302, and the inflatable volume 301.

The first piston 120 includes a first piston head 122. A one-way valve 140 having a valve inlet 106 and a valve outlet 107 is incorporated into the first piston head 122. The first piston head 122 includes annular first piston seals 126 that form a seal with the first piston bore 111, thereby forming a first piston chamber 104 when the first piston 120 is inserted into the first piston bore 111. The first piston chamber 104 is in fluid communication with the opening 103 and outlet 102. The first piston 120 encloses a cylindrical second piston bore 121 that is configured to receive the second piston 130. The second piston bore 121 extends along the length of the first piston 120.

The second piston 130 includes an actuation portion 132 and a second piston head 134. The actuation portion 132 may have any form suitable for actuating the second piston 130. The second piston head 134 includes annular second piston seals 136 that form a seal with the second piston bore 122, thereby forming a second piston chamber 108 when the second piston 130 is inserted into the second piston bore 121. Though the illustrated first and second piston chambers are cylindrical and are concentrically aligned, the pistons and piston chambers may be any suitable shape and do not need to be axially aligned.

The one-way valve 140 includes an opening 142 and a flange 144. The flange 144 is received in an annular groove 124 configured to receive the flange 144 so that the one-way valve is retained within the first piston head 122. In some embodiments, the one-way valve 140 is integrally formed with the first piston 120. The one-way valve 140 is shown as a flexible slit valve, but may be any kind of one-way valve, such as a ball and spring valve, a poppet valve, a flapper valve, an umbrella valve, a mushroom valve, a duck bill valve, or the like. The one-way valve 140 is oriented such that, under normal conditions, the valve 140 prevents flow into the first piston chamber 108 from the second piston chamber 104, and allows flow from the first piston chamber 108 into the second piston chamber 104 through a one-way valve outlet 107. That is, unless the one-way valve 140 is disabled, fluid is only allowed to flow from the first chamber into the second chamber. Also, fluid will only flow from the first chamber to the second chamber when pressure in the first chamber exceeds the pressure in the second chamber.

Referring now to FIG. 9, the inflator 100 is shown in a fully charged condition. When the inflator 100 is in the fully charged condition, the inflatable device 300 and expandable device 310 are in a compressed condition. In the fully charged condition, the first and second pistons 120, 130 are withdrawn to starting positions proximate the open ends of the first and second piston bores 111, 121, respectively, and the first and second piston chambers 104, 108 are filled with actuation fluid. The inflator 100 is actuated by applying force to the actuation portion 132 of the second piston 130 while holding the flange 112 of the inflator body 110 to move the first and second pistons 120, 130 thereby compressing the first and second piston chambers 104, 108 to discharge actuation fluid through the outlet 102. The inflator 100 is discharged in two stages, each corresponding to the actuation of one of the two pistons 120, 130.

Referring now to FIG. 10, the inflator 100 is shown in a partially discharged condition; i.e., after completing the first discharge stage by fully actuating the first piston 120. As can be seen by comparing FIGS. 9 and 10, movement from the charged position to the partially discharged position increases the inflated volume 301 of the inflatable device 300. When the inflator 100 is in the partially discharged condition, the inflatable device 300 is partially inflated and expandable device 310 is partially expanded. Discharge of the first piston 120 is accomplished by applying actuation force to the actuation portion 132 of the second piston. During actuation of the first piston 120, the fluid contained in the second piston chamber 108 is trapped by the one-way valve 140, thereby preventing the second piston 130 from actuating.

As can be seen in FIG. 10, the opening protrusion 116 is shaped to protrude through the valve opening 106 in the first piston head 122 to open the valve opening 142 of the one-way valve 140. That is, the protrusion 116 holds the one-way valve 140 open, allowing fluid to flow in either direction—into or out of the chamber 108. In the illustrated embodiment, the one-way valve 140 is a slit-valve formed from an elastic and flexible material that is capable of being stretched open by the opening protrusion 116 to open the valve opening 142. In certain embodiments, the opening protrusion is a portion of the first piston head that is biased away from the one-way valve with springs that are compressed at the bottom of the stroke of the first piston, thereby allowing the opening protrusion to open the one-way valve. In certain embodiments, the one-way valve is a spring-loaded poppet valve having a poppet that is opened when a protrusion extending from the poppet engages the inflator housing at the bottom of the stroke of the first piston.

Once the opening protrusion 116 (or other structure) has engaged the one-way valve 140 in the first piston head 122, further movement of the pistons 120, 130 causes the opening protrusion 116 to open the one-way valve 140. The one-way valve 140 is fully opened at the end of the actuation stroke of the first piston 120. Opening of the one-way valve 140 allows fluid in the second piston chamber 108 to be discharged, thereby automatically transitioning the inflator 100 between the first and second discharge stages. Thus, both of the first and second pistons 120, 130 of the inflator 100 can be fully actuated (as shown in FIG. 11) in a single application of force to the actuation portion 132 of the second piston 130. When the inflator 100 is fully discharged, the inflatable device 300 and expandable device 310 are fully expanded. As can be seen by comparing FIGS. 10 and 11, movement from the partially discharged position to the fully discharged position increase the volume 301 of the inflatable device 300.

The second piston 130 has a smaller diameter and consequently a smaller cross-sectional area than the first piston 120. Thus, the force required to actuate the inflator 100 during actuation of the first piston 120 is greater than the force required to actuate the second piston 130. The volume of the first and second piston chambers 104, 108 is determined by the diameter of the piston bores 111, 121 and the length of the chambers 104, 108. Thus, the maximum volume of each chamber 104, 108 may be altered by altering the length and diameter of the bores 111, 121. The volume of the first piston chamber 104 may be greater than, substantially equal to, or less than the volume of the second piston chamber 108. In some embodiments, the first piston chamber 104 has a volume that is substantially equal to the volume of the second piston chamber 108 so that substantially the same volume of fluid is displaced by the actuation of the second piston 130 relative to the first piston 120. In some embodiments, the second piston chamber 108 has less volume than the first piston chamber 104, so that less fluid is displaced by the actuation of the second piston 130 relative to actuation of the first piston 120. In certain embodiments, the force required to actuate the second piston 130 is about 5 percent to about 75 percent, or about 5 percent to about 50 percent, or about 5 percent to about 25 percent, or about 10 percent of the force required to actuate the first piston 120.

Figure 12:
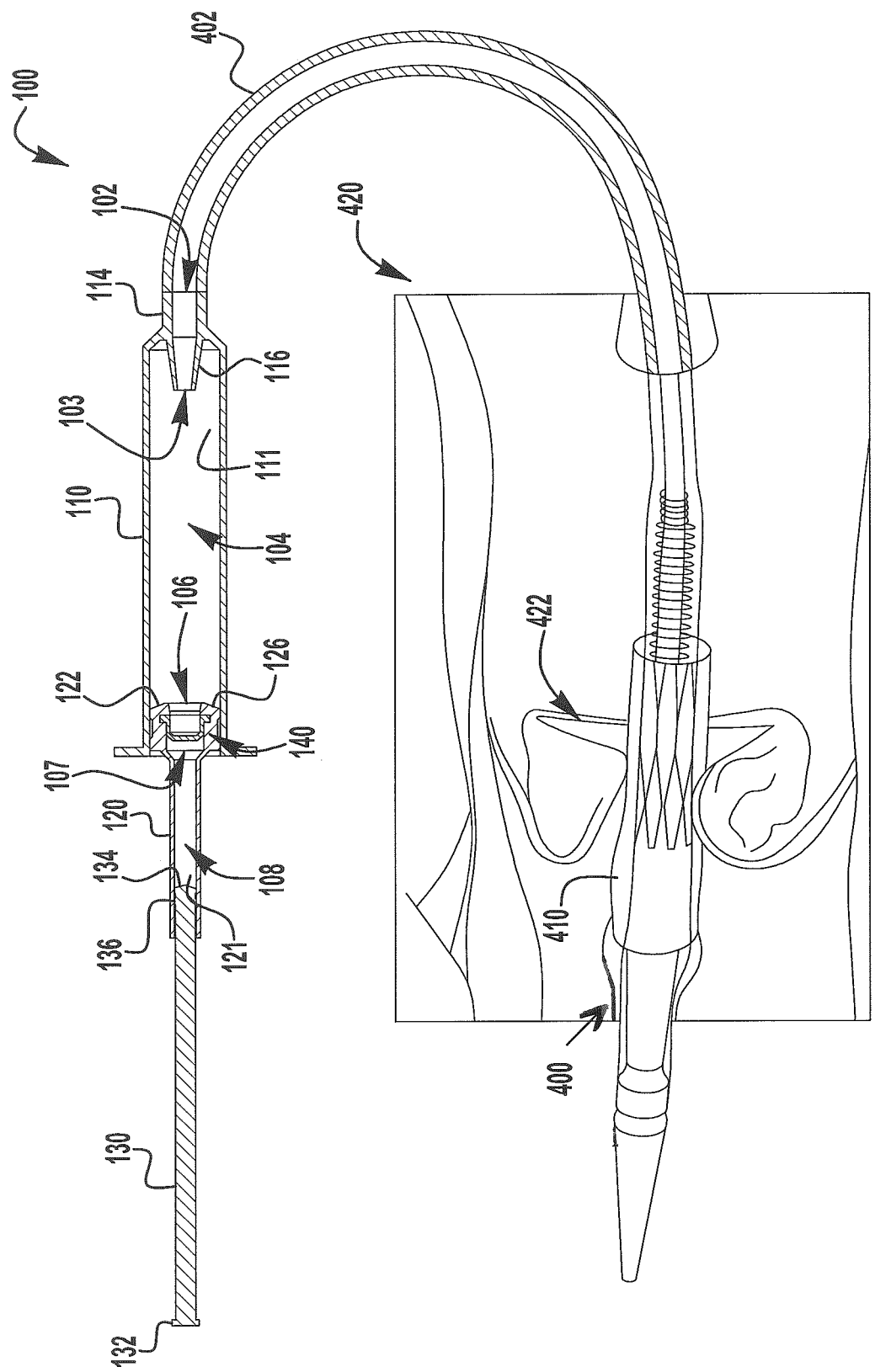
FIG. 12 is a cross-section view of an exemplary inflator in a fully charged condition attached to an inflatable device in a fully deflated condition inside of an implantable device being delivered and implanted within a native heart valve.
Figure 13:
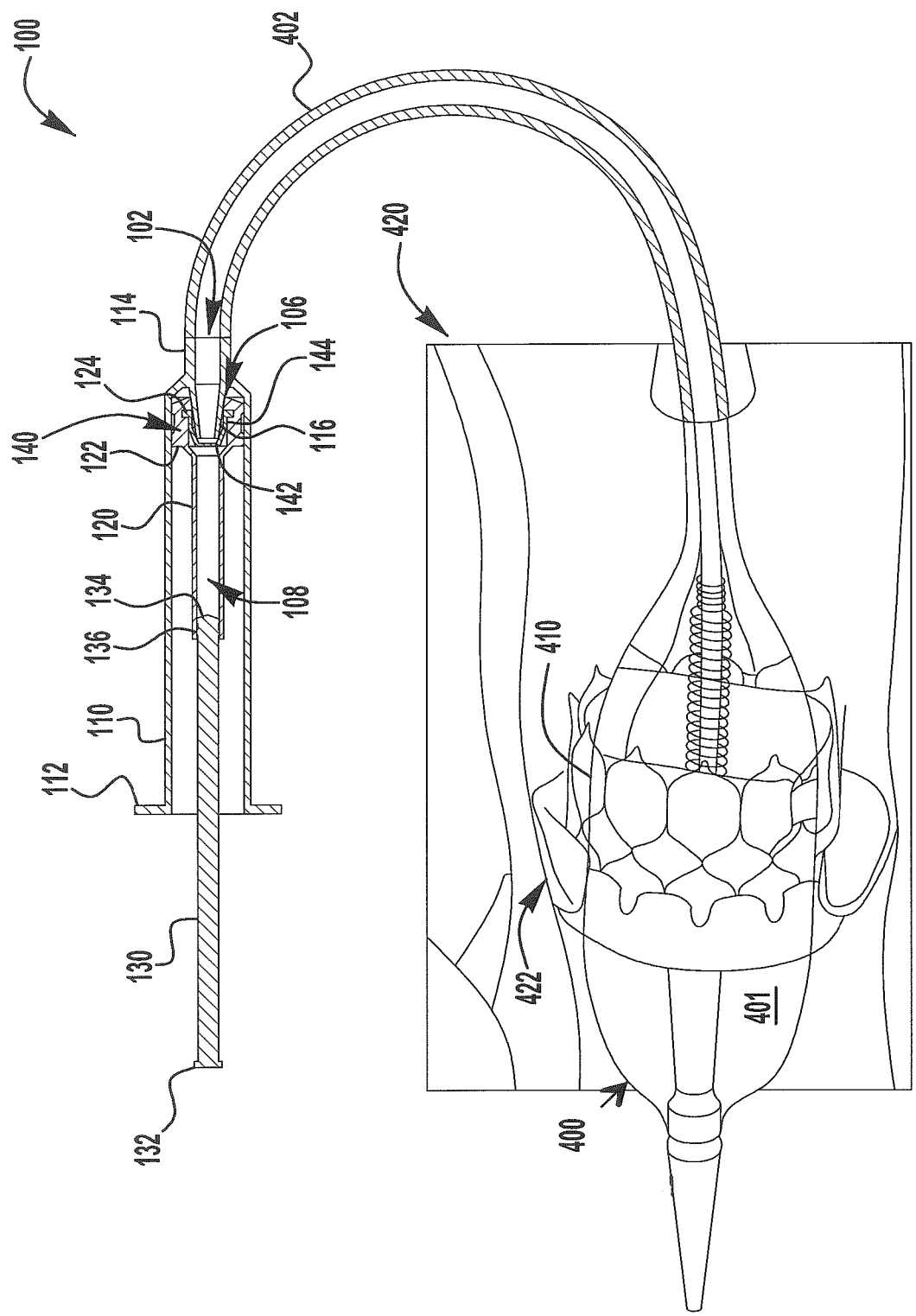
FIG. 13 is a cross-section view of an exemplary inflator in a partially discharged condition attached to an inflatable device in a partially inflated condition inside of an implantable device being delivered and implanted within a native heart valve.
Figure 14:
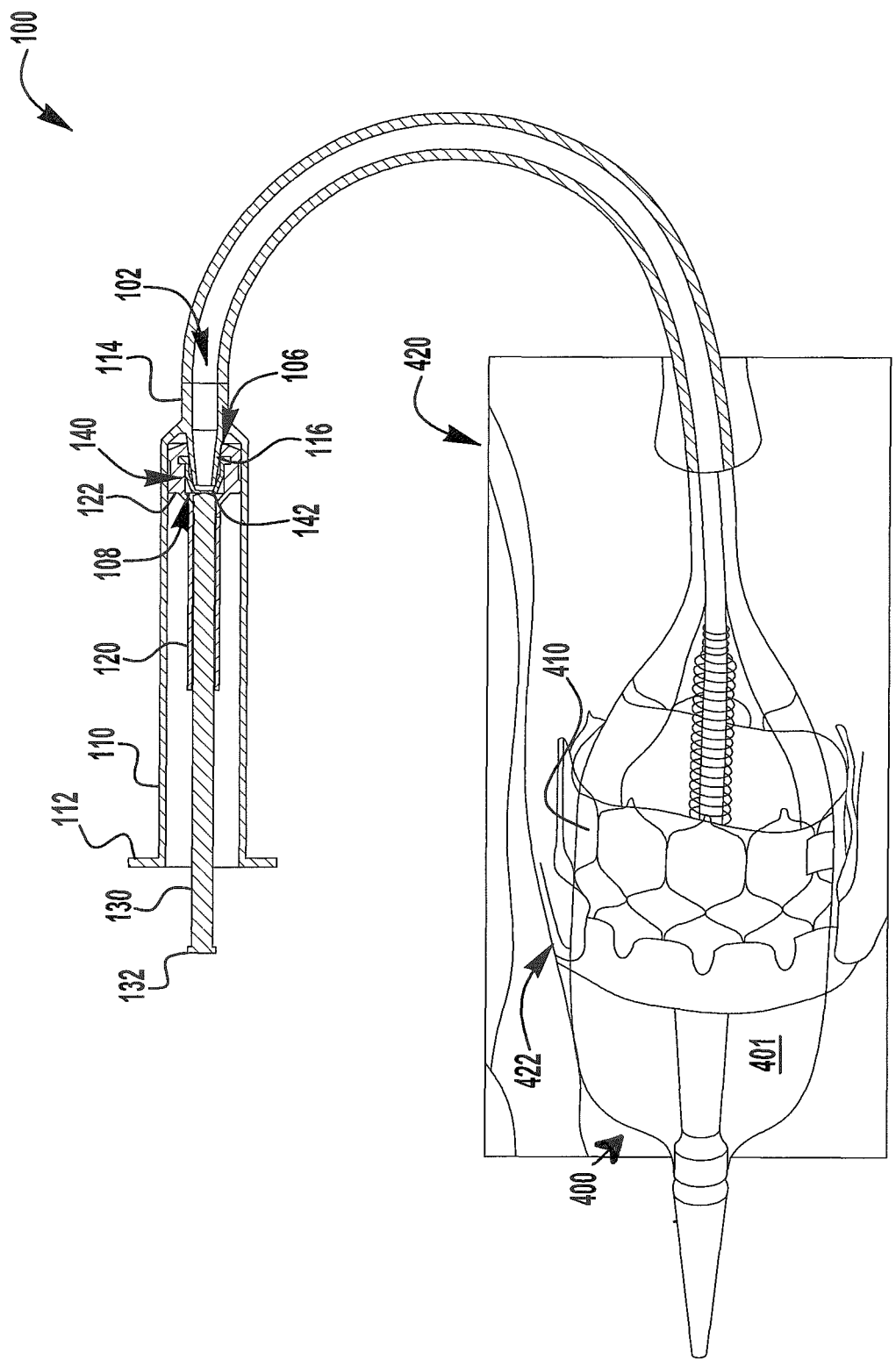
FIG. 14 is a cross-section view of an exemplary inflator in a fully discharged condition attached to an inflatable device in a fully inflated condition inside of an implantable device being delivered and implanted within a native heart valve.

Referring now to FIGS. 12-14 an exemplary inflator 100 is shown attached to an inflatable device 400 enclosing an inflatable volume 401. The inflator 100 has an inflator body 110, a first piston 120, and a second piston 130. The inflator body 110 includes an actuation flange 112 and a nozzle 114. The actuation flange 112 can be located at any position along the exterior of the inflator body 110. The nozzle 114 is attached to a tube 402 in fluid communication with the inflatable device 400 to be inflated by the inflator 100. The inflatable device 400 is disposed within an expandable medical device 410 to be expanded by inflation of the inflatable device 400. The expandable medical device 410 is disposed within a native heart valve 422 of a heart 420 of a patient. In certain embodiments, the tube 402 is integrally formed with the inflator 100. The inflator body 110 encloses a cylindrical first piston bore 111 that is configured to receive the first piston 120. The first piston bore 111 extends along the length of the inflator body 110. An annular opening protrusion 116 is located on the interior of the inflator body 110 and includes a central opening 103 in fluid communication with the outlet 102, the tube 402, and the inflatable volume 401.

The first piston 120 includes a first piston head 122. A one-way valve 140 having a valve inlet 106 and a valve outlet 107 is incorporated into the first piston head 122. The first piston head 122 includes annular first piston seals 126 that form a seal with the first piston bore 111, thereby forming a first piston chamber 104 when the first piston 120 is inserted into the first piston bore 111. The first piston chamber 104 is in fluid communication with the opening 103 and outlet 102. The first piston 120 encloses a cylindrical second piston bore 121 that is configured to receive the second piston 130. The second piston bore 121 extends along the length of the first piston 120.

The second piston 130 includes an actuation portion 132 and a second piston head 134. The actuation portion 132 may have any form suitable for actuating the second piston 130. The second piston head 134 includes annular second piston seals 136 that form a seal with the second piston bore 122, thereby forming a second piston chamber 108 when the second piston 130 is inserted into the second piston bore 121. Though the illustrated first and second piston chambers are cylindrical and are concentrically aligned, the pistons and piston chambers may be any suitable shape and do not need to be axially aligned.

The one-way valve 140 includes an opening 142 and a flange 144. The flange 144 is received in an annular groove 124 configured to receive the flange 144 so that the one-way valve is retained within the first piston head 122. In some embodiments, the one-way valve 140 is integrally formed with the first piston 120. The one-way valve 140 is shown as a flexible slit valve, but may be any kind of one-way valve, such as a ball and spring valve, a poppet valve, a flapper valve, an umbrella valve, a mushroom valve, a duck bill valve, or the like. The one-way valve 140 is oriented such that, under normal conditions, the valve 140 prevents flow into the first piston chamber 108 from the second piston chamber 104, and allows flow from the first piston chamber 108 into the second piston chamber 104 through a one-way valve outlet 107. That is, unless the one-way valve 140 is disabled, fluid is only allowed to flow from the first chamber into the second chamber. Also, fluid will only flow from the first chamber to the second chamber when pressure in the first chamber exceeds the pressure in the second chamber.

Referring now to FIG. 12, the inflator 100 is shown in a fully charged condition. When the inflator 100 is in the fully charged condition, the inflatable device 400 and expandable device 410 are in a compressed condition. In the fully charged condition, the first and second pistons 120, 130 are withdrawn to starting positions proximate the open ends of the first and second piston bores 111, 121, respectively, and the first and second piston chambers 104, 108 are filled with actuation fluid. The inflator 100 is actuated by applying force to the actuation portion 132 of the second piston 130 while holding the flange 112 of the inflator body 110 to move the first and second pistons 120, 130 thereby compressing the first and second piston chambers 104, 108 to discharge actuation fluid through the outlet 102. The inflator 100 is discharged in two stages, each corresponding to the actuation of one of the two pistons 120, 130.

Referring now to FIG. 13, the inflator 100 is shown in a partially discharged condition; i.e., after completing the first discharge stage by fully actuating the first piston 120. As can be seen by comparing FIGS. 12 and 13, movement from the charged position to the partially discharged position increases the inflated volume 401 of the inflatable device 400. When the inflator 100 is in the partially discharged condition, the inflatable device 400 is partially inflated and expandable device 410 is partially expanded. Discharge of the first piston 120 is accomplished by applying actuation force to the actuation portion 132 of the second piston. During actuation of the first piston 120, the fluid contained in the second piston chamber 108 is trapped by the one-way valve 140, thereby preventing the second piston 130 from actuating.

As can be seen in FIG. 13, the opening protrusion 116 is shaped to protrude through the valve opening 106 in the first piston head 122 to open the valve opening 142 of the one-way valve 140. That is, the protrusion 116 holds the one-way valve 140 open, allowing fluid to flow in either direction—into or out of the chamber 108. In the illustrated embodiment, the one-way valve 140 is a slit-valve formed from an elastic and flexible material that is capable of being stretched open by the opening protrusion 116 to open the valve opening 142. In certain embodiments, the opening protrusion is a portion of the first piston head that is biased away from the one-way valve with springs that are compressed at the bottom of the stroke of the first piston, thereby allowing the opening protrusion to open the one-way valve. In certain embodiments, the one-way valve is a spring-loaded poppet valve having a poppet that is opened when a protrusion extending from the poppet engages the inflator housing at the bottom of the stroke of the first piston.

Once the opening protrusion 116 (or other structure) has engaged the one-way valve 140 in the first piston head 122, further movement of the pistons 120, 130 causes the opening protrusion 116 to open the one-way valve 140. The one-way valve 140 is fully opened at the end of the actuation stroke of the first piston 120. Opening of the one-way valve 140 allows fluid in the second piston chamber 108 to be discharged, thereby automatically transitioning the inflator 100 between the first and second discharge stages. Thus, both of the first and second pistons 120, 130 of the inflator 100 can be fully actuated (as shown in FIG. 14) in a single application of force to the actuation portion 132 of the second piston 130. When the inflator 100 is fully discharged, the inflatable device 400 and expandable device 410 are fully expanded. As can be seen by comparing FIGS. 13 and 14, movement from the partially discharged position to the fully discharged position increase the volume 401 of the inflatable device 400.

The second piston 130 has a smaller diameter and consequently a smaller cross-sectional area than the first piston 120. Thus, the force required to actuate the inflator 100 during actuation of the first piston 120 is greater than the force required to actuate the second piston 130. The volume of the first and second piston chambers 104, 108 is determined by the diameter of the piston bores 111, 121 and the length of the chambers 104, 108. Thus, the maximum volume of each chamber 104, 108 may be altered by altering the length and diameter of the bores 111, 121. The volume of the first piston chamber 104 may be greater than, substantially equal to, or less than the volume of the second piston chamber 108. In some embodiments, the first piston chamber 104 has a volume that is substantially equal to the volume of the second piston chamber 108 so that substantially the same volume of fluid is displaced by the actuation of the second piston 130 relative to the first piston 120. In some embodiments, the second piston chamber 108 has less volume than the first piston chamber 104, so that less fluid is displaced by the actuation of the second piston 130 relative to actuation of the first piston 120. In certain embodiments, the force required to actuate the second piston 130 is about 5 percent to about 75 percent, or about 5 percent to about 50 percent, or about 5 percent to about 25 percent, or about 10 percent of the force required to actuate the first piston 120.

While various inventive aspects, concepts and features of the disclosures may be described and illustrated herein as embodied in combination in the exemplary embodiments, these various aspects, concepts, and features may be used in many alternative embodiments, either individually or in various combinations and sub-combinations thereof. Unless expressly excluded herein all such combinations and sub-combinations are intended to be within the scope of the present application. Still further, while various alternative embodiments as to the various aspects, concepts, and features of the disclosures—such as alternative materials, structures, configurations, methods, devices, and components, alternatives as to form, fit, and function, and so on—may be described herein, such descriptions are not intended to be a complete or exhaustive list of available alternative embodiments, whether presently known or later developed. Those skilled in the art may readily adopt one or more of the inventive aspects, concepts, or features into additional embodiments and uses within the scope of the present application even if such embodiments are not expressly disclosed herein.

Additionally, even though some features, concepts, or aspects of the disclosures may be described herein as being a preferred arrangement or method, such description is not intended to suggest that such feature is required or necessary unless expressly so stated. Still further, exemplary or representative values and ranges may be included to assist in understanding the present application, however, such values and ranges are not to be construed in a limiting sense and are intended to be critical values or ranges only if so expressly stated.

Moreover, while various aspects, features and concepts may be expressly identified herein as being inventive or forming part of a disclosure, such identification is not intended to be exclusive, but rather there may be inventive aspects, concepts, and features that are fully described herein without being expressly identified as such or as part of a specific disclosure, the disclosures instead being set forth in the appended claims. Descriptions of exemplary methods or processes are not limited to inclusion of all steps as being required in all cases, nor is the order that the steps are presented to be construed as required or necessary unless expressly so stated. The words used in the claims have their full ordinary meanings and are not limited in any way by the description of the embodiments in the specification.

What is claimed is:

1. A system comprising:
   a catheter;
   an inflatable device coupled to the catheter;
   an expandable device coupled to the inflatable device;
   an inflator coupled to the catheter, the inflator comprising:
   an inflator body comprising a first piston chamber, an opening protrusion disposed within the first piston chamber, and a nozzle in fluid communication with the first piston chamber;
   a first piston comprising a first piston head and a second piston chamber, the first piston head comprising a piston seal, a valve, and a valve opening; and
   a second piston comprising a second piston head and an actuation portion;

wherein the valve is in fluid communication with the first piston chamber and with the second piston chamber; and wherein movement of the first piston causes the opening protrusion to engage and open the valve; and wherein the inflatable device is disposed inside the expandable device and is in fluid communication with the inflator so that inflation of the inflatable device by the inflator expands the expandable device.

2. The system according to claim 1, wherein the expandable device is a prosthetic heart valve.

3. The system according to claim 1, wherein the expandable device is a stent.

4. The system according to claim 1, wherein opening the valve with the opening protrusion allows the second piston to actuate.

5. The system according to claim 1, wherein the inflatable device is attached to the nozzle of the inflator by the catheter.

6. The system according to claim 1, wherein a diameter the first piston is greater than a diameter of the second piston.

7. The system according to claim 1, wherein the valve is a check valve.

8. The system according to claim 1, wherein one of the first and second pistons is prevented from actuating when the other of the first and second pistons is being actuated.

9. The system according to claim 1, wherein the opening protrusion has an annular frustoconical shape having a central opening.

10. The system according to claim 9, wherein the central opening is axially aligned with an outlet of the nozzle.

11. The system according to claim 1, wherein a first volume of the first piston chamber is greater than a second volume of the second piston chamber.

12. The system according to claim 1 wherein a first actuation force required to actuate the first piston is greater than a second actuation force required to actuate the second piston, and a first actuation pressure during actuation of the first piston is less than a second actuation pressure during actuation of the second piston.

13. A method of expanding an expandable device, the method comprising:
providing a system comprising:
a catheter;
an inflatable device coupled to the catheter;
an expandable device coupled to the inflatable device;
wherein the inflatable device disposed within the expandable device; and an inflator in fluid communication with the inflatable device, the inflator comprising an inflator body, a first piston, and a second piston;
applying force to the second piston to sequentially push fluid out of the inflator body with the first piston, open a passage through the first piston, and push fluid through the first piston with the second piston to inflate the inflatable device and thereby expand the expandable device.

14. The method according to claim 13, wherein the second piston is prevented from moving in the first piston until fluid is pushed out of the inflator body with the first piston.

15. The method according to claim 13, wherein the expandable device is a prosthetic valve.

16. The method according to claim 15 wherein the prosthetic valve is expanded inside a native heart valve.

17. The method according to claim 13, wherein the expandable device is a stent.

18. A system comprising:
a catheter;
an inflatable device coupled to the catheter;
an expandable prosthetic valve coupled to the inflatable device;
an inflator coupled to the catheter, the inflator comprising:
an inflator body comprising a first piston chamber, an opening protrusion disposed within the first piston chamber, and a nozzle in fluid communication with the first piston chamber;
a first piston comprising a first piston head and a second piston chamber, the first piston head comprising a piston seal, a valve, and a valve opening; and
a second piston comprising a second piston head and an actuation portion;
wherein the valve is in fluid communication with the first piston chamber and with the second piston chamber; and
wherein movement of the first piston causes the opening protrusion to engage and open the valve; and
wherein
wherein the inflatable device disposed inside the expandable prosthetic valve;
wherein the inflatable device is connected to the nozzle by the catheter;
wherein inflation of the inflatable device by the inflator expands the expandable prosthetic valve.

* * * * *